(12) United States Patent
Suzuki et al.

(10) Patent No.: US 7,112,431 B2
(45) Date of Patent: Sep. 26, 2006

(54) 5-SUBSTITUTED HYDANTOIN RACEMASE, DNA CODING FOR THE RACEMASE, AND PROCESSES FOR PRODUCING OPTICALLY ACTIVE AMINO ACIDS

(75) Inventors: Shunichi Suzuki, Kanagawa (JP);
Norimasa Onishi, Kanagawa (JP);
Kenzo Yokozeki, Kanagawa (JP)

(73) Assignee: Ajinomoto Co. Inc., Tokyo (JP)

( * ) Notice: Subject to any disclaimer, the term of this patent is extended or adjusted under 35 U.S.C. 154(b) by 121 days.

(21) Appl. No.: 10/863,245

(22) Filed: Jun. 9, 2004

(65) Prior Publication Data

US 2005/0084946 A1 Apr. 21, 2005

Related U.S. Application Data

(62) Division of application No. 09/950,772, filed on Sep. 13, 2001, now Pat. No. 6,815,195.

(30) Foreign Application Priority Data

Sep. 13, 2000 (JP) ............... 2000-278571
Mar. 8, 2001 (JP) ............... 2001-65815

(51) Int. Cl.
*C12N 9/90* (2006.01)
*C12P 41/00* (2006.01)

(52) U.S. Cl. ..................... 435/233; 435/280
(58) Field of Classification Search ............ None
See application file for complete search history.

(56) References Cited

U.S. PATENT DOCUMENTS 5,516,660 A 5/1996 Wagner et al.
5,714,355 A 2/1998 Wagner et al.
6,551,795 B1 4/2003 Rubenfield et al.
2003/0148472 A1* 8/2003 Takenaka et al. .......... 435/106

FOREIGN PATENT DOCUMENTS

WO WO 01/23535 4/2001

OTHER PUBLICATIONS

JAPAN No. SHO 62-122591 (Abstract), (1987).
JAPAN No. HEI 6-343462 (Abstract), (1994).
JAPAN No. HEI 4-271764 (Abstract), Piltzsch, et al.
"A New Racemase for 5-Monosubstituted Hydantoins" Ann. N.Y. Acad. Sci. 672, 478-483 (1978).
K. Watabe, et al., Journal of Bacteriology, vol. 174, No. 24, pp. 7989-7995, XP-000944035, "Purification and Characterization of the Hydantoin Racemase of Pseudomonas, sp. Strain NS671 Expressed in *Escherichia col*", Dec. 1992.
A. Wiese, et al., Journal of Bacteriology, vol. 80, No. 3, pp. 217-230, XP-004214557, "Hydantoin Racemase From Arthobacter Aurescens DSM 3747" Heterologous Expression, Purification and Characterization, Jul. 14, 2000.
A.S. Bommarius, et al., Chirality, pp. 371-397, XP-000991099, "Membran Bioreactors for the Production of Enantiomerically Pure Alpha-Amino Acids", 1992.
Acc. No. AAV30458 (1998).
Sherman, D.H., et al. (1997) Acc. No. AAT68715.
Zhu, H., et al. (2000) Acc. No. AW714318.
Anderson, O.D., et al. (2000) Acc. No. BE605170.

* cited by examiner

*Primary Examiner*—Charles L. Patterson, Jr.
(74) *Attorney, Agent, or Firm*—Oblon, Spivak, McClelland, Maier & Neustadt, P.C.

(57) ABSTRACT

The present invention relates to a 5-substituted hydantoin racemase, which efficiently catalyzes racemization reactions at a high optimum temperature for racemization reactions, DNA coding for the racemase, and processes for producing optically active amino acids.

10 Claims, 5 Drawing Sheets

5-SUBSTITUTED HYDANTOIN RACEMASE, DNA CODING FOR THE RACEMASE, AND PROCESSES FOR PRODUCING OPTICALLY ACTIVE AMINO ACIDS

This application is a divisional of U.S. application Ser. No. 09/950,772, filed on Sep. 13, 2001, now U.S. Pat. No. 6,815,195 which claims priority to: JP 2000-278571, filed on Sep. 13, 2000 and JP 2001-65815, filed on Mar. 8, 2001.

FIELD OF THE INVENTION

The present invention relates to a 5-substituted hydantoin racemase, which efficiently catalyzes racemization reactions at a high optimum temperature for racemization reactions, DNA coding for the racemase, and processes for producing optically active amino acids.

BACKGROUND OF THE INVENTION

The 5-substituted hydantoin racemase enzyme (hereinafter abbreviated to HRase) catalyzes a racemization reaction of an optically active 5-substituted hydantoin compound, i.e., a D- or L-5-substituted hydantoin compound.

The 5-substituted hydantoin compound undergoes a hydrolysis reaction with hydantoinase (1) and Carbamyl amino acid hydrolase (2) to form an amino acid as shown in the following reaction scheme (I):

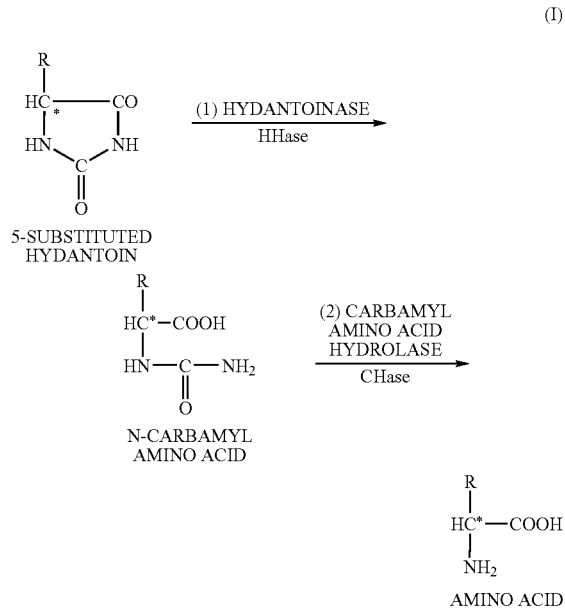

As shown in the reaction scheme above, the hydantoinase hydrolyzes the 5-substituted hydantoin compound thereby forming N-carbamyl amino acid. Additionally, the N-carbamyl amino acid hydrolase hydrolyzes N-carbamyl amino acid thereby forming an optically active amino acid. These enzymes should be optically selective.

Methods of using a microbial enzyme system and combining a bacterial enzyme system with a chemical reaction system have been previously described. Production of optically amino acids from 5-substituted hydantoin compounds is important in the production of pharmaceutical preparations, chemical industry products, food additives and other similar articles or products.

The optico-selective hydrolysis should enable the efficient racemization of one enantiomer to another enantiomer, the second enantiomer can further serve as a substrate, for example see the above reaction scheme. Furthermore, this conversion can be performed using microbial enzymes or microbial enzymes combined with a chemical reaction system. Under neutral conditions where the enzyme system is active, the racemization of the optically active 5-substituted hydantoin compound, not serving as the substrate, is very low. Therefore, the racemization becomes rate-determining and resulting in poor conversion into the optically active amino acid.

Accordingly, for the purpose of racemization of the optically active 5-substituted hydantoin compound under neutral conditions, HRase was searched for, and HRases derived from microorganisms of the genus *Arthrobacter* (Japanese Patent Application Laid-Open (JP-A) No. 62-122591; Ann. N. Y. Acad. Sci., 672, 478; Japanese Patent Application Laid-Open (JP-A) No. 6-343462) and microorganisms of the genus *Pseudomonas* (Japanese Patent Application Laid-Open (JP-A) No. 4-271784; J. Bacteriol., 174, 7989 (1992)) have been reported. The optimum reaction temperatures of the previously reported HRases derived from microorganisms are 37° C. for the enzyme derived from *Arthrobacter* sp. DSM-3747 (Ann. N. Y. Acad. Sci., 672, 478), 10 to 50° C. for the enzyme derived from *Arthrobacter* sp. DK200 (Japanese Patent Application Laid-Open (JP-A) No. 62-122591), and 45° C. for the enzyme derived from *Pseudomonas* sp. NS671.

Generally, when the working optimum temperature of an enzyme is increased, the industrial utility value of the enzyme is also increased. That is, if the reaction temperature can be increased, the reaction rate can be also increased, which results not only in efficient progress of the desired reaction but also in a reduction in the risk of contamination of the reaction solution with microorganisms during the reaction. This results in several advantages including easy process and quality control.

As described above, HRase having a higher optimum temperature for the reaction is useful from the viewpoint of industrial applicability. However, the upper limit of the working optimum temperatures of the previously reported HRases is 50° C. and an HRase having a higher working optimum temperature is desired to achieve efficient progress of the racemization reaction and to reduce the risk of contamination of the reaction solution with microorganisms.

SUMMARY OF THE INVENTION

It is an object of the present invention to isolate a novel HRase having a higher reaction optimum temperature than conventional and to provide a process for producing an optically active amino acid by use of the enzyme.

As a result of extensive study in view of the problem described above, the present inventors found a novel HRase having a desired higher reaction optimum temperature is present in a *Microbacterium* microorganism, thus arriving at completion of the present invention.

One object of the present invention, is providing a new process adjuvant for improving the racemization reaction of 5-substituted hydantoin compounds and optically active amino acids.

Another object of the invention is to provide a nucleotide sequence encoding a polypeptide which has HRase activity. One embodiment of such a sequence is the nucleotide sequence of SEQ ID NO: 1. Other embodiments include nucleotide sequences that are complimentary to the sequences described herein, those sequences that are 70%, 80% and/or 90% identical to the sequences described herein and/or those sequences that hybridize under stringent conditions to the sequences described herein.

A further object of the invention is a method of making HRase or an isolated polypeptide having a HRase activity, as well as use of such isolated polypeptides in the production of amino acids. One embodiment of such a polypeptide is the polypeptide having the amino acid sequence of SEQ ID NO: 2. Other embodiments are this polypeptide are those that are 70%, 80% and/or 90% identical to the amino acid sequences described herein. Another embodiment of the polypeptide is that which has racemase activity with an optimal working pH of from about 7 to about 9 and an optimal working temperature of from about 50 to about 60° C.

Other objects of the invention include methods of detecting nucleic acid sequences homologous to the sequences described herein, particularly nucleic acid sequences encoding polypeptides that have HRase activity, and methods of making nucleic acids encoding such polypeptides.

Another object of the present invention is to provide methods of preparing optically active hydantoin compounds by contacting a 5-substituted hydantoin compound with the HRase described herein.

Another object of the present invention is to provide methods of preparing an N-carbamyl amino acid by contacting a 5-susbstituted hydantoin compound with the HRase described herein and an enzyme that will hydrolyze the 5-substituted hydantoin compound in an optically selective manner. One embodiment of an enzyme that will hydrolyze the 5-substituted hydantoin compound is the Hydantoinase described herein. The Hydantoinase may have the amino acid sequence of SEQ ID NO:4 or amino acid sequences with substantial identity to SEQ ID NO:4 and having the hydantoinase activity.

Another object of the present invention is to provide methods of producing optically active amino acids by contacting a 5-substituted hydantoin compound with the HRase described herein, an enzyme that will hydrolyze the 5-substituted hydantoin compound in an optically selective manner, and an enzyme that will hydrolyze a N-carbamyl amino acid in an optically selective manner. One embodiment of an enzyme that will hydrolyze the 5-substituted hydantoin compound is the Hydantoinase described herein. The Hydantoinase may have the amino acid sequence of SEQ ID NO:4 or amino acid sequences with substantial identity to SEQ ID NO:4 and having the hydantoinase activity. One embodiment of the enzyme that will hydrolyze the N-carbamyl amino acid is the carbamyl amino acid hydrolase described herein. The carbamyl amino acid hydrolase may have the amino acid sequence of SEQ ID NO:6 or amino acid sequences with substantial identity to SEQ ID NO:6 and having the hydrolase activity.

The above objects highlight certain aspects of the invention. Additional objects, aspects and embodiments of the invention are found in the following detailed description of the invention.

DETAILED DESCRIPTION OF THE INVENTION

Figure 1:
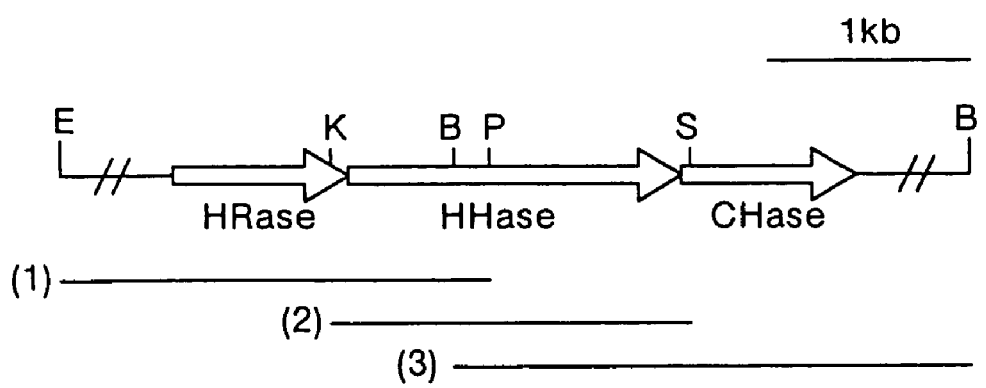
FIG. 1 is a drawing showing a group of structural genes coding for hydantoin racemase, hydantoinase and N-carbamyl-L-amino acid hydrolase.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Reference is made to standard textbooks of molecular biology that contain definitions and methods and means for carrying out basic techniques, encompassed by the present invention. See, for example, Maniatis et al., Molecular Cloning: A Laboratory Manual, Cold Spring Harbor Laboratory, New York (1982) and Sambrook et al., Molecular Cloning: A Laboratory Manual, Cold Spring Harbor Laboratory, New York (1989) and the various references cited therein.

[I] HRase

Among Flavobacterium microorganisms, a bacterial strain optico-selectively hydrolyzing DL-5-indolyl methyl hydantoin to form its corresponding L-tryptophan is reported. When this microbial strain (Flavobacterium sp. AJ3912 (FERM-P3133)) forming L-tryptophan is used in the reaction of forming L-tryptophan from DL-5-indolyl methyl hydantoin as the substrate, the molar yield of L-tryptophan formed reaches 80% or more (Agric. Biol. Chem., 51, 363 (1987)).

Since spontaneous racemization of optically active indolyl methyl hydantoin rarely occurs under neutral conditions where the enzyme reaction is carried out, it was presumed that a novel HRase is present in the microbial strain. On the basis of this presumption, the present inventors purified and isolated a HRase from a cultured microorganism. This novel enzymes was found to have a desired high optimum reaction temperature.

*Flavobacterium* sp. AJ3912 (FERM-P3133) was initially deposited as *Flavobacterium* sp. AJ3912 (FERM-P3133) on Jun. 27, 1975 with the National Institute of Bioscience and Human-Technology, the Agency of Industrial Science of Technology, the Ministry of International Trade and Industry, Japan, which was later reclassified as a *Microbacterium liquefaciens* microorganism. Thus, this microorganism is deposited as *Microbacterium liquefaciens* AJ3912 (FERM-P3133) with the National Institute of Bioscience and Human-Technology, the Agency of Industrial Science of Technology, the Ministry of International Trade and Industry.

The physiological properties of *Microbacterium liquefaciens* AJ3912 (FERM-P3133) were examined in light of a microbial classification book, Berjey's Manual of Determinative Bacteriology, Vol. 1 (9th edition, 1994, William & Wilkins Publishing Company), and the test results are shown in Table 1.

TABLE 1

Results of re-identification of *Microbacterium liquefaciens* AJ3912

| | |
|---|---|
| Gram stainability | positive |
| Motility | none |
| Nitrate reduction | − |
| Pyrimidinase | − |
| Pyridonyl allyl amidase | − |
| Alkali phosphatase | + |
| β-Glucuronidase | − |
| β-Galactosidase | + |
| α-Glucosidase | + |
| N-Acetyl-β-glucosaminidase | + |
| Aesculin (glucosidase) | + |
| Urease | − |
| Gelatin liquefaction | + |
| Fermentability of hydrocarbons | |
| glucose | − |
| ribose | − |
| xylose | − |
| mannitol | − |
| maltose | − |
| lactose | − |
| white sugar | − |
| glycogen | − |
| Anaerobic growth | − |
| Casein hydrolyzability | + |

The present inventors purified HRase derived from *Microbacterium liquefaciens* AJ3912, and the amino acid sequence of the HRase was determined. From this amino acid sequence an approximately 30-bp DNA molecule was synthesized and used as to probe a *Microbacterium* chromosomal library. This resulted in the successful isolation a full-length DNA that codes for the *Microbacterium* HRase.

Further, the present inventors predicted that a nucleotide sequence downstream from the HRase gene, which was simultaneously obtained in isolation of the HRase is a part of a hydantoinase (HHase) gene. Thus, this DNA fragment was amplified by PCR and utilized as a probe to successfully isolate the Hhase gene. The present inventors also predicted that a nucleotide sequence downstream from the HHase gene, which was simultaneously obtained in isolation of the HHase gene, is a part of an N-carbamyl amino acid hydrolase (CHase) gene. Thus, this DNA fragment was amplified by PCR and utilized as a probe to successfully isolate the Chase gene.

As shown in FIG. 1, the HRase gene of the present invention is considered to form an operon together with the HHase gene and CHase gene. In FIG. 1, (1) is an EcoRI/PstI fragment, (2) is a KpnI/SacI fragment, and (3) is a BglII fragment.

In the accompanying sequence listing of the present invention, the DNA coding for the HRase of the present invention is shown in SEQ ID NO:1, the DNA coding for the HHase is shown in SEQ ID NO:3, and the DNA coding for the CHase is shown in SEQ ID NO:5, as determined by the method described above. Further, DNA coding for a group of structural genes including the HRase gene, HHase gene and CHase gene is set forth in SEQ ID NO:7. In the nucleotide sequence set forth in SEQ ID NO:7, the nucleotide residues 1 to 708 code for the HRase of the present invention, the nucleotide residues 729 to 2105 code for the HHase, and the nucleotide residues 2105 to 3340 code for the CHase.

These DNAs were those isolated from the chromosomal DNA in *Microbacterium liquefaciens* AJ3912 and code for proteins related to the production of L-amino acids.

Further, the amino acid sequence of the HRase encoded by the nucleotide sequence in SEQ ID NO:1 in the Sequence Listing is set forth in SEQ ID NO:2 in the Sequence Listing, the amino acid sequence of the HHase encoded by the nucleotide sequence in SEQ ID NO:3 in the Sequence Listing is set forth in SEQ ID NO:4 in the Sequence Listing, and the amino acid sequence of the CHase encoded by the nucleotide sequence in SEQ ID NO:5 in the Sequence Listing is set forth in SEQ ID NO:6 in the Sequence Listing.

As shown in the reaction scheme below, the HRase having the sequence of SEQ ID NO:2 g, the Hhase having the sequence of SEQ ID NO:4 and the CHase having the sequence of SEQ ID NO:6 catalyze the reaction of coverting a 5-substituted hydantoin (5-(4-hydroxylbenzyl)hydantoin) to an optically active amino acid (e.g., L-tyrosine) as shown in the reaction scheme (II) below:

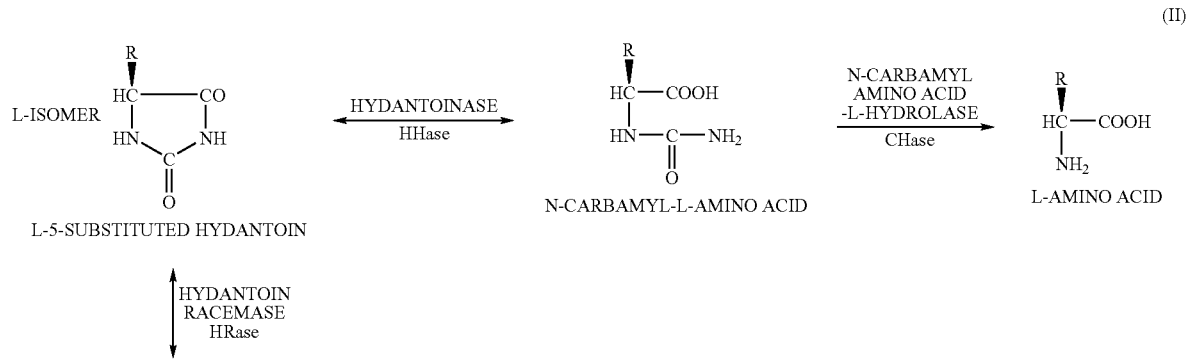

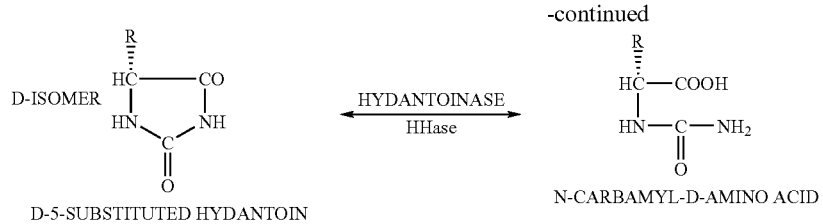

D-5-SUBSTITUTED HYDANTOIN ⇌ (HYDANTOINASE / HHase) ⇌ N-CARBAMYL-D-AMINO ACID (1) DNA Coding for the HRase Enzyme As described above, the present HRase gene having the nucleotide sequence of SEQ ID NO:1 was isolated from the chromosomal DNA of *Microbacterium liquefaciens* AJ3912. The amino acid sequence of SEQ ID NO:2 and the nucleotide sequence of SEQ ID NO:1 exhibit 48% homology in the amino acid sequence and 49% homology in the nucleotide sequence to a known HRase derived from a *Pseudomonas* microorganism (J. Bacteriol. 174, 962 (1992)).

The method of acquiring DNA coding for the HRase from the microorganism of the genus *Microbacterium* is described below.

First, the amino acid sequence of the purified HRase is determined. The amino acid sequence can be determined by use of the Edman method (Edman, P., Acta Chem. Scand. 4, 227 (1950)). Alternatively, the amino acid sequence can be determined by use of a sequencer manufactured by Applied Biosystems. By determining the amino acid sequence of 30 residues from the N-terminus in the HRase of the present invention derived from the *Microbacterium* microorganism, the sequence shown in SEQ ID NO:8 was determined.

Based on this amino acid sequence, the nucleotide sequence of DNA coding for the same can be deduced using the universal codons known in the art.

Based on the deduced nucleotide sequence, a DNA molecule of approximately 30-bp is synthesized. The method of synthesizing the DNA molecule is disclosed in Tetrahedron Letters, 22, 1859 (1981). Alternatively, the DNA molecule can be synthesized by use of a synthesizer manufactured by Applied Biosystems. The DNA molecule can be used as a probe so that full-length DNA coding for the HRase is isolated from a *Microbacterium* chromosomal gene library. Alternatively, the DNA molecule can be used as a primer by which DNA coding for the HRase is amplified by PCR. However, if the amplified DNA amplified does not contain a full-length coding DNA, the amplified DNA may be used as a probe to obtain the full-length coding DNA from a *Microbacterium* chromosomal gene library.

PCR amplification is known in the art and is described, for example, in White, T. J. et al., in Trends Genet. 5, 185 (1989). The method of preparing chromosomal DNA and the method of isolating the desired DNA molecule from a gene library by use of the above DNA molecule as a probe are described are known in the art and described in, for example, Molecular Cloning, 2nd edition, Cold Spring Harbor Laboratory Press, Cold Spring Harbor, N.Y.(1989).

The method of determining the nucleotide sequence of the isolated DNA coding for the HRase is generally known in the art and described, for example, in A Practical Guide to Molecular Cloning, John Wiley.& Sons, Inc., New York (1985). Alternatively, the nucleotide sequence can be determined by use of a DNA sequencer manufactured by Applied Biosystems. The DNA coding for the *Microbacterium* HRase is shown in SEQ ID NO:1.

The DNA molecules encoding *Microbacterium* HRase is not limited to the DNA set forth in SEQ ID NO:1 in the Sequence Listing. This is because the nucleotide sequence must be varied depending on the species and strain of each *Microbacterium* microorganism.

As a matter of course, the DNA of the present invention encompasses not only the isolated DNA coding for the HRase but also HRase-coding DNA which can be prepared by artificially mutating the HRase-coding DNA isolated from the chromosomal DNA in the microorganism of the genus *Microbacterium*. For example, site-specific mutagenesis methods as known in the art and described, for example, in Methods in Enzymology, 154 (1987).

The DNA of the present invention also encompasses DNA having a nucleotide sequence hybridizing under stringent conditions with the nucleotide sequence set forth in SEQ ID NO:1 in the Sequence Listing and coding for a protein having a 5-substituted hydantoin racemase activity. As used herein, "stringent conditions" refer to those conditions under which a specific hybrid is formed whereas an unspecific hybrid is not formed. These conditions will vary depending on the nature, length, base content, etc. of the DNA.

Specificity is typically the function of post-hybridization washes, the critical factors being the ionic strength and temperature of the final wash solution. For DNA-DNA hybrids, the $T_m$ can be approximated from the equation of Meinkoth and Wahl, Anal. Biochem., 138:267–284 (1984): $T_m = 81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with approximately 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C.

(formamide solution) it is preferred to increase the SSC concentration so that a higher temperature can be used. An extensive guide to the hybridization of nucleic acids is found in Tijssen, Laboratory Techniques in Biochemistry and Molecular Biology—Hybridization with Nucleic Acid Probes, Part I, Chapter 2 "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Interscience, New York (1995).

For example, stringent conditions will allow hybridization between DNA molecules having higher homology, for example 50% or more, more preferably 70%, more preferably 80% or more and most preferably 90% or more. Under these stringent conditions DNA molecules having lower homology would not hybridize with each other, or to those conditions under which hybridization occurs under usual washing conditions in Southern hybridization, that is, at 60° C., a salt concentration of 1×SSC and 0.1% SDS, preferably at 60° C., 0.1×SSC and 0.1% SDS and more preferably at 65° C., 0.1×SSC and 0.1% SDS.

The "5-substituted hydantoin racemase activity" may be any activity of racemizing a 5-substituted hydantoin compound. However, the nucleotide sequence hybridizing under stringent conditions with the nucleotide sequence set forth in SEQ ID NO:1 in the Sequence Listing preferably maintain about at least half of the enzyme activity of a protein having the amino acid sequence set forth in SEQ ID NO:2 in the Sequence Listing under reaction conditions of 50° C. and pH 8 and as described herein.

The DNA of the present invention also encompasses DNA coding for substantially the same protein as the HRase encoded by the DNA set forth in SEQ ID NO:1. That is, the DNA of the present invention encompasses DNA coding for a protein having a 5-substituted hydantoin racemase activity and having the following amino acid sequence:

(a) the amino acid sequence set forth in SEQ ID NO:2 in the Sequence Listing, or (b) an amino acid sequence wherein in the amino acid sequence set forth in SEQ ID NO:2 in the Sequence Listing, one or more amino acid residues have been replaced, deleted, inserted, added or inverted. Here, the number of "one or more amino acid residues" is in such a range that the stereostructure of the proteins of amino acid residues or the 5-substituted hydantoin racemase activity is not significantly deteriorated; specifically, the number of such amino acids is 2 to 50, preferably 2 to 30 and more preferably 2 to 10. However, the amino acid sequence (b) wherein in the amino acid sequence set forth in SEQ ID NO:2 in the Sequence Listing, one or more amino acid residues have been replaced, deleted, inserted, added or inverted, preferably has about at least half of the enzyme activity of a protein having the amino acid sequence set forth in SEQ ID NO:2 under reaction conditions of 50° C. and pH 8. Furthermore, the invention also encompasses DNA encoding proteins having the aforementioned activity and which are substantionally identical to SEQ ID NO:2, preferably at least 70%, 80%, 90% or 95% identical.

(2) Properties of HRase

As revealed by isolation and analysis of the above-described gene, the HRase of the present invention has the amino acid sequence set forth in SEQ ID NO:2. However, the present invention also encompasses a protein having a 5-substituted hydantoin racemase activity and having an amino acid sequence wherein in the amino acid sequence set forth in SEQ ID NO:2 in the Sequence Listing, one or more amino acid residues have been replaced, deleted, inserted, added or inversed.

That is, the HRase of the present invention is a protein having a 5-substituted hydantoin racemase activity and having the following amino acid sequence (a) or (b):

(a) the amino acid sequence of SEQ ID NO:2, and (b) an amino acid sequence wherein in the amino acid sequence of SEQ ID NO:2, one or more amino acid residues have been replaced, deleted, inserted, added or inverted.

The terms "one or more amino acid residues" and "5-substituted hydantoin racemase activity" have the same meanings as defined in item (1) DNA coding for HRase. Also included within the scope of the present invention are those proteins that have the herein described racemization activity and have 70%, preferably 80%, more preferably 90% or 95% identity with the amino acid sequence of SEQ ID NO:2.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482–489 (1981), to find the best segment of identity or similarity between two sequences. Gap performs global alignments: all of one sequence with all of another similar sequence using the method of Needleman and Wunsch, J. Mol. Biol. 48:443–453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The HRase of the present invention catalyzes the racemization reaction of a 5-substituted hydantoin compound.

Measurement of the HRase activity of the HRase of the present invention can be carried out by measuring a change in the optical rotation as the degree of racemization of the optically active D- or L-5-substituted hydantoin compound as the substrate or by high performance liquid chromatography (HPLC) using an optical resolution column.

Specifically, a reaction solution containing 120 mg/dl L- or D-benzyl hydantoin (BH), 50 mM dibasic potassium phosphate buffer (KPB) (pH 8.0), 5 mM dithiothreitol (DTT) and an HRase enzyme solution was incubated at 37° C. for 30 minutes, and the reaction was stopped by adding a 9-fold excess volume of 1.1 mM $CuSO_4$ and 11.1 mM $H_3PO_4$ solution. The precipitates were removed by centrifugation at 20,000 g×10 minutes, and the amount of racemized BH was quantitatively determined by HPLC to estimate the racemization activity. The enzyme activity causing racemization of 1 μmol BH per minute under these conditions was defined as 1 U of the enzyme activity.

The quantitative analysis of optically active BH by analysis in HPLC was conducted by use of Daicel Chemical CHIRALPAK WH 0.46 cmϕ×25 cm. The analysis conditions are as follows:

Mobile phase: 5% (v/v) methanol, 1 mM $CuSO_4$
Column temperature: 50° C.
Flow rate: 1.5 ml/min.

Detection: $UV_{210}$

Under these conditions, D-BH (retention time: 4.2 minutes) and L-BH (retention time: 5.3 minutes) were eluted.

Then, the enzymatic chemical properties of the HRase of the present invention measured by the above analysis method are described below.

The working optimum temperature of the HRase of the present invention lies in a higher temperature range than that of the previously reported HRases, and thus the present enzyme is characterized by the ability to catalyze racemization reactions efficiently. That is, the HRase of the present invention are characterized as having a working optimum temperature, though varying at a certain degree due to a difference in the amino acid sequence, of 50° C. or more, preferably 52° C. or more, more preferably 55° C. or more. The upper limit of the working optimum temperature is not particularly limited, but in consideration of the thermostability of HRase, the upper limit is preferably 60° C. or less. The "working optimum temperature" in the present specification means the temperature at which the maximum activity is exhibited under at pH 8.

To determine the range of the working optimum pH, the reaction was carried out for 30 minutes under the condition of 40° C. The optimum pH was determined to be from approximately 7 to approximately 9.

The pH stability after treatment at each pH for 30 minutes under the condition of 0° C. was examined. The pH stability was determined to be from approximately 6 to approximately 9.

The temperature stability after heating treatment for 30 minutes under the condition of pH 8.0 was examined and was determined to be approximately 40° C. or less. The HRase of the present invention is strongly inhibited by NEM (N-ethyl maleimide), copper ion, or IAA (monoiodoacetatic acid) but minimally inhibited by EDTA (ethylenediaminetetraacetic acid). The HRase of the invention is activated by adding DTT (dithiothreitol) The Molecular weight of the HRase of the present invention: a) about 107,000 determined by gel filtration, or b) about 27,000 determined on a SDS-PAGE. Based on these results it is believed that the HRase of the present invention is a tetramer, where each subunit of the tetramer has a molecular weight of approximately 27,000.

(3) Process for Producing HRase and a Protein Having a 5-Substituted Hydantoin Racemase Activity The process for producing the HRase of the invention and a protein having a 5-substituted hydantoin racemase activity includes two methods, that is, (i) a process which comprises culturing a microorganism to form and accumulate HRase, and (ii) a process of transforming a microorganism with a gene encoding HRase or a protein having a 5-substituted hydantoin racemase activity by recombinant DNA technology and culturing the transformant to form and accumulate the protein.

(i) Process of Formation and Accumulation by Culturing a Microorganism

The microorganim culturing methods preferably employ a *Microbacterium* HRase. Preferable microorganisms include *Microbacterium liquefaciens* AJ3912 (FERM-P3133).

The form of culture of *Microbacterium* microorganisms may be either liquid culture or solid culture, but an industrially advantageous method is a submerged aeration shake culture method. Nutrient sources in the liquid medium can make use of carbon sources, nitrogen sources, inorganic salts and other trace nutrient sources, which are usually used in culture of microorganisms. Any nutrient sources can be used insofar as they can be utilized by the bacterial strain cultured.

As the aeration conditions, aerobic conditions are preferably used. The culture temperature may be in any range in which the microorganism grows and produces HRase. Accordingly, there are no strict conditions, but the culture temperature is usually 10 to 50° C., preferably 30 to 40° C. The culture time is varied depending on other culture conditions. For example, the microorganism may be cultured until most of the HRase is produced, and the culture time is usually 5 hours to 7 days, preferably 10 hours to 3 days or thereabout.

Following culturing the enzyme can be obtained by collecting the microorganisms by centrifugation (e.g., 10,000×g, 10 minutes). Because the enzyme is present in the microorganism, this microorganism may be disrupted or lysed to faciliate solublization of the enzyme. Methods of disrupting cells are known in the art and include, for example, sonication, French press, glass beads, treatment with egg white lysozyme or peptidase enzymes, or suitable combinations of two or more of these methods.

To purify-the HRase, the solubilized enzyme is used as the starting material, and if undisrupted or non-lyzed microbial residues are present, it is advantageous to centrifuge the solubilized solution again to remove the precipitated residues.

For purification of the enzyme, enzyme purification methods known in the art can be employed. Such methods include, for example, salting-out with ammonium sulfate, gel filtration, ion-exchange chromatography, hydrophobic chromatography, and other types of chromatography or purification methods. As a result, a fraction containing HRase of higher specific activity can be obtained.

(ii) Recombinant DNA Methods

Figure 2:
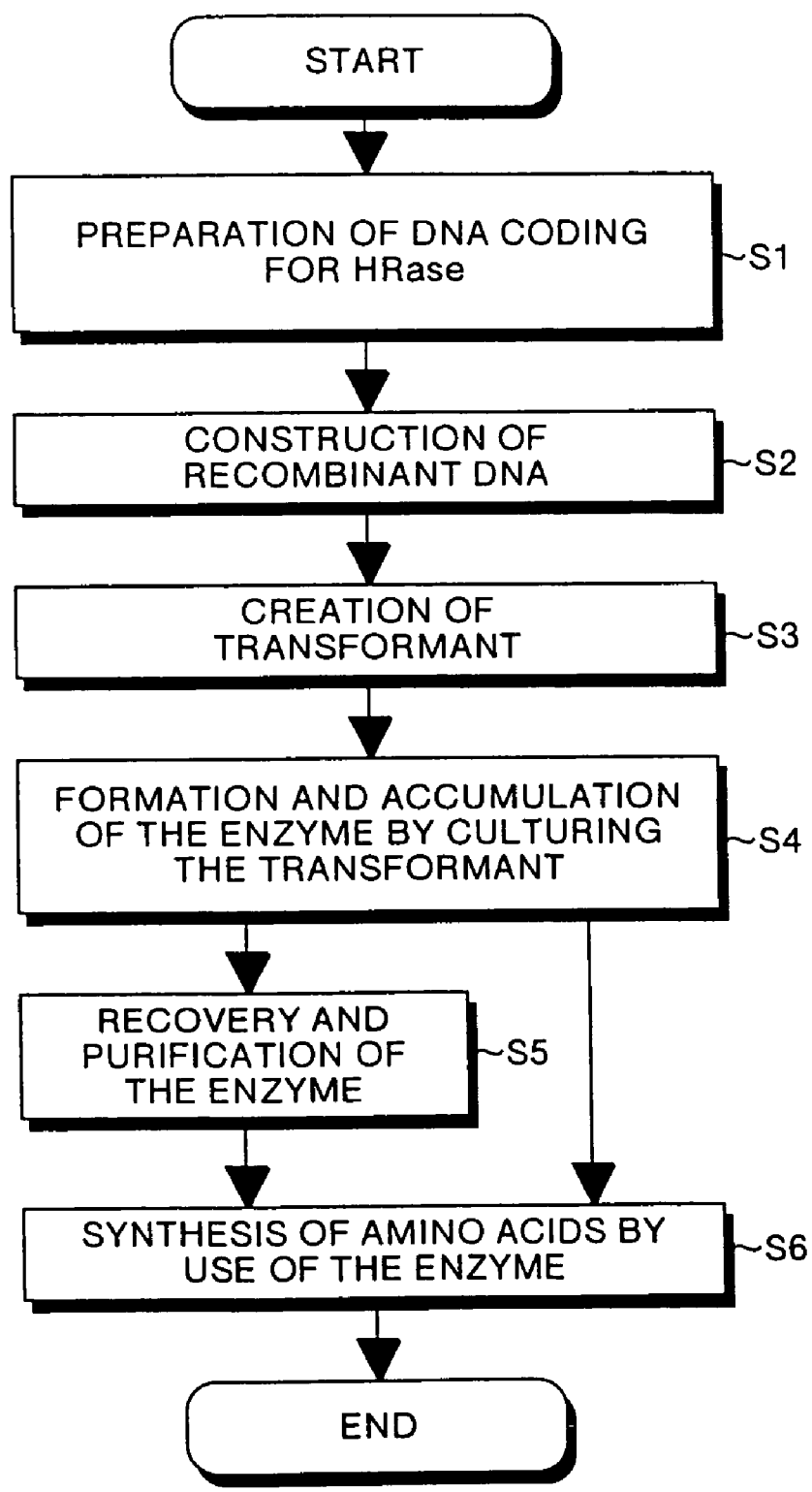
FIG. 2 is a flow chart showing a process for producing the hydantoin racemase of the present invention.

The enzymes of the present invention can be advantageously prepared using recombinant DNA technology commonly employed in the art to faciliate scaling up the amount of enzyme produced by a microorganism and thus the amount of active enzyme obtained from the microorganism culturing methods described herein. An example of such methods is shown in FIG. 2 is a flow chart of the process for producing the HRase of the present invention.

First, the DNA coding for the HRase of the present invention is prepared (step S1).

Then, the prepared DNA is ligated to a vector DNA to prepare a recombinant DNA (step S2), and cells are transformed with the recombinant DNA, to prepare a transformant (step S3). Subsequently, the transformant is cultured in a medium to form and accumulate HRase in the medium and/or the cells (step S4).

Thereafter, the enzyme is recovered and purified in step S5.

Further, the purified HRase produced in step S5 or the medium containing the HRase in step S4 can be used in the synthesis of large amounts of optically active amino acids (step S6).

The DNA ligated to the vector DNA may be any DNA capable of expressing the HRase of the present invention. The HRase encoding DNAs ligated into the vector DNA include any of the DNA molecules described herein.

When the protein production is scaled up to yield large quantities of protein, the protein may aggregate in the transformant to form a protein inclusion body. The formation of protein inclusion bodies provides the advantage of protecting the protein in the microorganism from proteolyitc digestion in the cell and faciliates simpler purification following centrifugation and cell disruption as described above. To obtain the active protein from the protein inclusion body, a series of procedures such as solubilization and activity restoration etc. are necessary, and thus the procedures are more complex than in direct production of the active protein. However, if a protein-exerting an influence on growth of the microorganism is produced in a large amount in the microorganism, the influence can be suppressed by accumulating the protein as an inert inclusion body in the microorganism.

The protein inclusion body may be solubilized with a protein denaturant and renatured by removing the denaturant, for example, by dialysis. Following renaturation the activity of the protein is restored, as described for the restoration of the activity of human interleukin-2 (Japanese Patent Application Laid-Open (JP-A) No. 61-257931).

The method of producing a large amount of the desired protein as an inclusion body includes not only a method of expressing the desired protein solely under the control of a strong promoter but may also include expressing the protein as a fusion protein to facilate purification. Preferably, when preparing the fusion protein a sequence recognized by a proteolytic enzyme is provided between the HRase and the peptide or polypeptide to which is fused. This proteolytic enzyme sequence facilitates separation of the HRase from the fusion peptide or polypeptide after purification. Examples of such proteolytic enzymes blood coagulation factor Xa or kallikrein whose recognition sequence is a sequence not present in HRase.

The host cells to be transformed for producing a large amount of the protein by recombinant DNA technology include microbial cells, Actinomyces cells, yeast cells, fungal cells, plant cells, animal cells etc., but in general *Escherichia coli* is preferably used. This is because there are a large number of techniques for a large production of proteins by use of *Escherichia coli*.

As the promoter expressing DNA coding for HRase, a promoter ordinarily used in production of a heterogeneous protein in *E. coli* can be used or other promoters as appropriate to express the protein in the specific cell employed for expression. Examples of such promoters include strong promoters such as the T7 promoter, trp promoter, lac promoter, tac promoter, PL promoter and the like.

To produce HRase as a fusion protein inclusion body, a gene coding for another protein, preferably a hydrophilic peptide, is ligated to a region upstream or downstream of the HRase gene to produce a fusion-protein gene. The gene coding for another protein may be any gene which increases the amount of a fusion protein accumulated and raises the solubility of the fusion protein after denaturation and restoration, and for example, T7 gene 10, β-galactosidase gene, dehydrofolate reductase gene, interferon γ gene, interleukin-2 gene, prochymosin gene may be used.

When ligating the two genes together, the coding readings should be kept in-frame to insure appropriate translation of the fusion protein. They may be ligated at suitable restriction enzyme sites, or synthetic DNA of suitable sequence may be utilized.

To increase the amount of the fusion protein produced, a terminator that is a transcription termination sequence is preferably ligated to a downstream region of the fusion-protein gene. Examples of such terminators include T7 terminator, fd phage terminator, T4 terminator, a terminator for tetracycline resistance gene, a terminator for *E. coli* trp A gene, and similar terminators as known to the skilled artisan.

Vectors for introducing the HRase gene or HRase fusion protein into *E. coli* are preferably multicopy vectors. Examples of such vectors includes plasmids having an origin of replication derived from Col E1: pUC series plasmids, pBR322 series plasmids or derivatives thereof. The "derivatives thereof" are those obtained by modifying plasmids by replacement, deletion, insertion, addition or inversion of some nucleotides. The modification referred to here includes modification by natural mutation or by mutation treatment with a mutagen or UV irradiation.

To select the transformant, the vector preferably has a marker or drug resistance genes known in the art. Examples of such drug resistance genes include ampicillin resistance gene, kanamycin resistance gene, tetracyline resitance gene and the similar genes. As such plasmids, expression vectors having a strong promoter are commercially available (pUC series (Takara Shuzo Co., Ltd.), PPROK series (Clontech), pKK233-2 (Clontech) etc.).

A DNA fragment having a promoter, a gene coding-for HRase or a fusion protein of HRase with another protein and a terminator ligated in this order is then ligated to a vector DNA to give a recombinant DNA.

The recombinant DNA is used to transform *E. coli* or other microorganism and the HRase or a fusion protein of HRase with another protein is expressed and produced upon culturing the transformed cell.

Although the host to be transformed can be any strain ordinarily used for expressing a heterogeneous gene, *Escherichia coli* JM109, particularly *Escherichia coli* JM109 (DE3) is prefered. The method for conducting transformation and the method for selecting the transformant are described in, for example, Molecular Cloning, 2nd edition, Cold Spring Harbor Press (1989).

The production medium used may be a medium such as M9-casamino acid medium, LB medium etc. which is usually used for culturing *E. coli*. Other appropriate media depending on the cell being cultured can be formulated as known in the art. Further, culture conditions and production-inducing conditions are selected suitably depending on a marker and a promoter in the vector used, the type of host microorganism, and other factors that the skilled artisan would recognize.

To recover HRase or a HRase fusion protein the following may be employed. If HRase or its fusion protein has been solubilized, the microorganism is recovered, disrupted or lyzed and the resulting crude enzyme solution can be used. As necessary, HRase or its fusion protein can be used in a pure form after purification as described herein. In this case, a method of purification by use of an antibody against HRase or its fusion protein can also be used. Methods of making antibodies reactive against HRase are known in the art and are described in, for example, Harlow and Lane, Antibodies: A Laboratory Manual, Cold Spring Harbor Laboratory Press, Cold Spring Harbor, N.Y. (1989).

When the protein inclusion body is formed, it is solubilized with a denaturant. The inclusion body may be solubilized together with microbial proteins, but in consideration of the subsequent purification procedures, it is preferable that the inclusion body is removed and solubilized. The inclusion body can be recovered from the microorganism by a method known in the art. For example, the microorganism is disrupted and centrifuged etc. to recover the inclusion body. The denaturant for solubilizing the protein inclusion body includes guanidine hydrochloride (e.g., 6 M, pH 5 to 8) and urea (e.g. 8 M).

By removing the denaturant by dialysis, the activity of HRase is obtained. The dialysis solution used in dialysis may make use of Tris-HCl buffer or phosphate buffer, and a prefered concentration is 20 mM to 0.5 M, and a prefered pH is 5 to 8.

The concentration of the protein in the regeneration step is preferably limited to about 500 μg/ml or less. To prevent self-crosslinkage of the regenerated HRase, the dialysis temperature is preferably 5° C. or less. Further, the method of removing the denaturant includes a dilution method and an ultrafiltration method besides the dialysis method, and using any method, restoration of the activity can be expected.

If the DNA set forth in SEQ ID NO: 1 in the Sequence Listing is used as DNA coding for HRase, HRase having the amino acid sequence set forth in SEQ ID NO:2 is produced.

[II] Process for Producing an Optically Active Amino Acid by HRase

The HRase of the present invention used in the reaction of producing an optically active amino acid includes a protein having a hydantoin racemase activity and has an amino acid sequence as described herein.

As the HRase, it is possible to use (1) HRase obtained by culturing a *Miccrobacterium* microorganism or (2) by preparing an HRase-producing transformant as described herein.

When a *Microbacterium* microorganism transformed with HRase is used, a substrate may be added directly to a culture during or after culturing or any material containing the enzyme which includes, lysed or disrupted cells, crude enzyme preparations, enzyme preparations at any stage of the purfication process and/or purified enzyme.

In the process for producing an optically active amino acid according to the present invention, the HRase of the present invention is combined with two other enzymes:(l) hydantoinase (Hhase), which hydrolyzes a 5-substituted hydantoin compound to form N-carbamyl amino acid, and (2) N-carbamyl amino acid hydrolase (CHase), which hydrolyzes N-carbamyl amino acid to form an optically active amino acid.

In the above, if the optical selectivity of HHase hydrolyzing a 5-substituted hydantoin compound is high, either optically active N-carbamyl-L-amino acid or N-carbamyl-D-amino acid can be formed in higher yields (50% or more molar yield by the action of HRase) by allowing the HHase having high optical selectivity and the HRase of the present invention to act on the 5-substituted hydantoin. In this case, CHase or a material containing the enzyme may be subsequently used to produce the optically active amino acid, or the optically active amino acid can be produced in higher yields while maintaining optical activity by chemical hydrolysis treatment with nitrite (combination of microbial enzyme and chemical reaction systems).

HHase as used for optico-selective hydrolyses of 5-substituted hydantoin compounds can be obtained in the following manner. For example, the presence of a thermostable D-HHase enzyme in *Bacillus* microorganisms having D-HHase forming N-carbamyl-D-amino acid is known; for example, HHase or an HHase-containing fraction may be prepared from *Bacillus stearothermophilus* ATCC 31195. (Appl. Microbiol. Biotechnol., 43, 270 (1995)), ATCC 31195 has been deposited at the American Type Culture Collection, 12301 Parklawn Drive, Rockville, Md. 20852, United States of America. Further, the presence of L-HHase acting specifically on L-hydantoin compounds is known in e.g. *Bacillus* sp. AJ12299 (Japanese Patent Application Laid-Open (JP-A) No. 63-24894). *Bacillus* sp. AJ12299 is a microorganism deposited on Jul. 5, 1986 under FERM-P8837 with the National Institute of Bioscience and Human-Technology, the Agency of Industrial Science of Technology, the Ministry of International Trade and Industry.

Even if D- has no optico-selective hydrolysis activity, the formed amino acid will be a D- or L-optically active isomer insofar as CHase has optical selectivity. In this case, decomposition of N-carbamyl-L-amino acid by Chase to form and L-amino acid, N-carbamyl-D-amino acid will remain in the reaction solution, as wells as when D-amino acids are formed. When this occurs, Hhase will catalyze the reverse reation of dehydrating and condensing N-carbamyl amino acids as the remaining unreacted enantioner, albeit at a lower rate than the forward reaction. This reverse reaction forms the 5-substituted hydantoin compound again, and therefore the optically active amino acid can be produced in high yield (at least 50% molar yield by the action of HRase) by the three enzymes, that is, HRase, HHase and highly optically selective CHase, or material(s) containing the three enzymes.

The presence of HHase having no optical selectivity in e.g. *Arthrobacter aurescens*, besides *Microbacterium liquefaciens* AJ3912 shown in the present invention, is known (J. Biotechnol. 61, 1 (1998)).

The presence of CHase selectively hydrolyzing a D-isomer of N-carbamyl amino acid in e.g. *Pseudomonas* sp. AJ 11220 is known (Japanese Patent Application Publication (JP-B) No. 56-003034). As a result of our re-classification, *Psudomonas* sp. AJ1122 is classified as *Agrobacterium* sp. *Agrobacterium* sp. AJ 11220 is a microorganism deposited on Dec. 20, 1977 under FERM-P4347 with the National Institute of Bioscience and Human-Technology, the Agency of Industrial Science of Technology, the Ministry of International Trade and Industry. Further, the presence of CHase selectively hydrolyzing an L-isomer of N-carbamyl amino acid in e.g. *Flavobacterium* sp. AJ3912 (Japanese Patent Application Publication (JP-B) No. 56-008749) and *Bacillus* sp. AJ12299 is known. As described above, *Flavobacterium* sp. AJ3912, which is now classified into *Microbacterium liquefaciens* AJ3912 (FERM-P3133), is a microorganism deposited on Jun. 27, 1975 under FERM-P3133 with the National Institute of Bioscience and Human-Technology, the Agency of Industrial Science of Technology, the Ministry of International Trade and Industry. Further, *Bacillus* sp. AJ12299 is a microorganism deposited on July 5, 1986 under FERM-P8837 with the National Institute of Bioscience and Human-Technology, the Agency of Industrial Science of Technology, the Ministry of International Trade and Industry.

The substrate of HRase or a fraction containing HRase can make any 5-substituted hydantoin compound which can be racemized with the substrate specificity of the enzyme. Examples of the 5-substituted hydantoin compound include 5-indolyl methyl hydantoin, 5-(p-hydroxybenzyl) hydantoin, 5-isobutyl hydantoin, 5-(3'-pyridyl)-methyl hydantoin and other similar hydantoin compounds.

A preferable combination of HRase, HHase and CHase includes a combination of: HRase having the amino acid sequence of SEQ ID NO:2, HHase having the amino acid sequence of SEQ ID NO:4, and CHase having the amino acid sequence of SEQ ID NO:6. These enzymes are preferably derived from *Microbacterium liquefaciens* AJ3912.

When HRase having the amino acid sequence set forth in SEQ ID NO:2 in the Sequence Listing, HHase having the S amino acid sequence in SEQ ID NO:4 in the Sequence Listing and CHase having the amino acid sequence in SEQ ID NO:6 in the Sequence Listing are used in combination, mixed proteins consisting of HRase, HHase and CHase, obtained by culturing cells transformed with a recombinant DNA comprising a vector ligated to a group of structural genes set forth in SEQ ID NO: 7 coding for all the proteins involved in producing L-amino acid can also be used. If the mixed proteins are used, the hydantoin racemase contained in the mixed proteins catalyses racemization of the 5-substituted hydantoin compound as shown in the reaction scheme (II) below, so that from the DL-5-substituted hydantoin compound, L-amino acid can be produced in theoretically 100% molar yield.

The formed amino acid can be separated and purified by techniques known in the art. Examples of such separation and purification protocols include adsorbing the basic amino acid by contacting with an ion-exchange resin, then eluting it followed by crystallization thereof, a method of discoloring the amino acid by filtration with activated carbon and then crystallizing it, etc. Other appropriate protocols can be employed.

Having generally described this invention, a further understanding can be obtained by reference to certain spe-

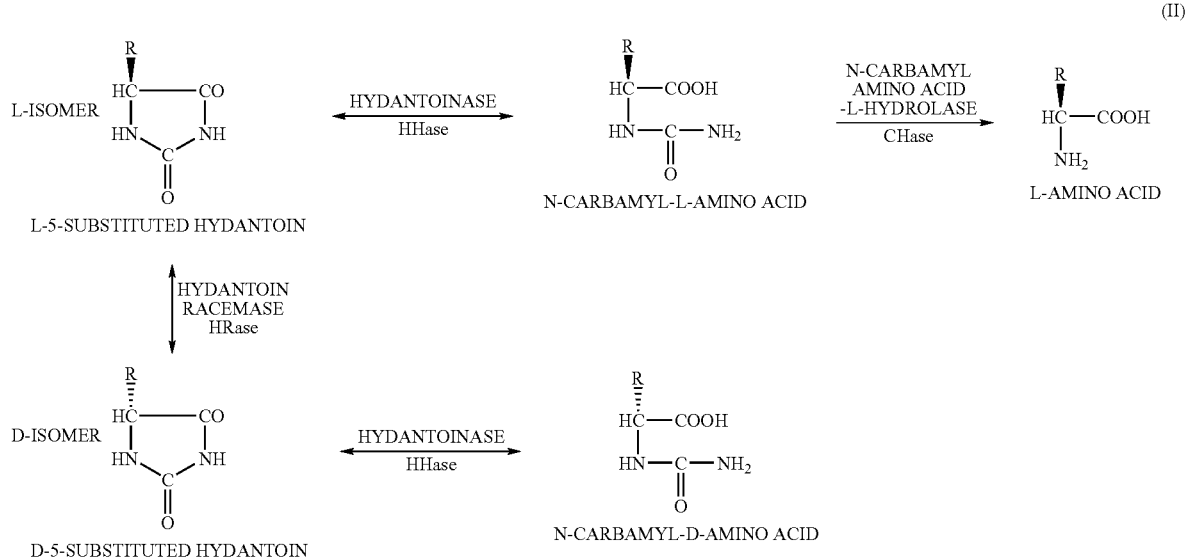

(II)

The above mixed proteins can also be used to produce N-carbamyl amino acids. For example, N-carbamyl amino acid can be produced by adding e.g. an inhibitor of the N-carbamyl-L-amino acid hydrolase to terminate the hydrolysis reaction at the stage of N-carbamyl amino acid.

When the HRase on any of the forms described herein is used in the amino acid forming reaction the reaction solution is preferably adjusted to a suitable temperature of from about 25 to about 40° C. is incubated for about 8 hours to about 5 days while maintaining the pH of the solution at 5 to 9. The incubation can performed with or without stirring, shaking or agitation. Preferably, the culture is performed under aerobic conditions.

When the amino acid forming reaction is performed in culture, the water-soluble medium used in the culture would contain a 5-substituted hydantoin compound and nutrients such as a carbon source, a nitrogen source and inorganic ions necessary for growth of the transformed cells as described herein. Preferably, the culture medium also contains organic trace nutrients such as vitamins, amino acids, and other nutrients that facilate cell growth and expression of the enzymes. The 5-substituted hydantoin compound may be added to the culture medium all at the same time, at the start of the culture or at some point during or after the culturing, the 5-substituted hydantoin compound may be added gradually to the culture, continuously, in a gradient (increasing concentrations or decreasing concentrations) or batch-wise to the culture.

cific examples, which are provided herein for purposes of illustration only, and are not intended to be limiting unless otherwise specified.

EXAMPLES

Example 1

Production and Purification of HRase

*Microbacterium liquefaciens* AJ3912 (FERM-P3133) was cultured to give the microorganism having a sufficient HRase activity.

First, the microorganism was refreshed at 30° C. for 24 hours in CM2G agar medium (0.5 g/dl D-glucose, 1 g/dl yeast extract, 1 g/dl peptone, 0.5 g/dl NaCl, 2 g/dl agar, pH 7.0), followed by seed culture in CM2G liquid medium at 30° C. for 24 hours.

Thereafter, 1 ml seed culture liquid was inoculated into a 500-ml Sakaguchi flask containing 50 ml main culture medium and cultured under shaking at 30° C. for 18 hours. The main culture medium was prepared by autoclaving a medium of 0.5 g/dl D-glucose, 0.5 g/dl $(NH_4)_2SO_4$, 1 g/dl yeast extract, 1 g/dl peptone, 0.1 g/dl $KH_2PO_4$, 0.3 g/dl $K_2HPO_4$, 0.01 g/dl $MgSO_4.7H_2O$, 0.35 g/dl DL-5-indolyl methyl hydantoin (IMH), pH 7.0, at 120° C. for 20 minutes, and then adding 1 mg/dl each of $FeSO_4.7H_2O$, $MnSO_4.4–5H_2O$, and $CaCl_2.2H_2O$ thereto and leaving the medium at 4° C. to precipitate IMH sufficiently.

After culture, the microorganism was collected by centrifugation, washed with 0.1 M KPB (pH 7.0) to give the washed microorganism.

The microorganism thus obtained was used as a material from which HRase was to be purified.

1. Disruption of the Microorganism 66 g of the washed microorganism (corresponding to 3.7 L culture liquid) was used as the starting material, and this microorganism was suspended in 130 ml of 0.1 M KPB (pH 7.0) and disrupted with 0.1 mmφ glass beads for 3 minutes (30 seconds×6 times at 90-second intervals) with a bead beater. The solution was recovered and treated with DNase I at a final concentration of 5 µg/ml at room temperature for 20 minutes. Thereafter, the undisrupted cells were removed by centrifugation at 13,000 g×10 minutes, and the membrane fraction was further removed by ultracentrifugation at 100,000 g×60 minutes, and the supernatant was used as a cell-free extract.

2. Ammonium Sulfate Fractionation 59 g ammonium sulfate was added at a final concentration of 70% saturation to 125 ml of the cell-free extract, and the extract was adjusted to pH 7.0 with KOH and stirred at 5° C. for 60 minutes. The precipitates were recovered by centrifugation at 13,000 g×15 minutes, dissolved in a small amount of 20 mM KPB (pH 7.0) and dialyzed against 1.2 M $(NH_4)_2SO_4$, 20 mM KPB, 0.5 mM $CoCl_2$, pH 7.0 (Buffer A). After dialysis, the dialyzate was centrifuged at 13,000 g×30 minutes, and the resulting supernatant, 40 ml, was used in the following purification.

3. Hydrophobic Chromatography

The resulting enzyme solution was subjected to a hydrophobic chromatography column Phenyl Superose HP 26/10 (Pharmacia) previously equilibrated with Buffer A. The non-adsorbed protein was eluted with Buffer A, and then the adsorbed protein was eluted with a linear gradient (−1.2 M/12 CV) of from 1.2 to 0 M ammonium sulfate. When the HRase activity of each eluted fraction was measured, the activity was recognized in elution positions of from about 500 mM to 100 mM ammonium sulfate. Fractions with the HRase activity were recovered, concentrated through a membrane and dialyzed against 20 mM KPB (pH 7.0).

4. Anion-Exchange Chromatography

The resulting enzyme solution was applied onto an anion-exchange chromatography column Q-Sepharose HP 16/10 (Pharmacia) previously equilibrated with 20 mM KPB (pH 7.0). After the non-adsorbed protein was eluted with 20 mM KPB (pH 7.0), the adsorbed protein was eluted with a linear gradient (0.5 M/12 CV) of from 0 to 0.5 M NaCl. When the HRase activity of each eluted fraction was measured, the activity was recognized in elution positions of from about 300 mM to 400 mM NaCl. Fractions with the HRase activity were recovered and concentrated through a membrane.

5. Gel Filtration

The resulting enzyme solution was applied onto Superdex 200 pg 16/60 (Pharmacia) previously equilibrated with 20 mM KPB (pH 7.0), and the sample was developed with the same buffer. When the HRase activity of each eluted fraction was measured, the activity was recognized at the position of an estimated molecular weight of about 107,0000. Fractions with the HRase activity were recovered, concentrated through a membrane and dialyzed against 1.0 M $(NH_4)_2SO_4$, 20 mM KPB, 1 mM L-benzyl hydantoin (BH), pH 7.0 (Buffer B).

6. Hydrophobic Chromatography

The resulting enzyme solution was applied onto Phenyl Superose 5/5 (Pharmacia) previously equilibrated with Buffer B. The non-adsorbed protein was eluted with Buffer B, and then the adsorbed protein was eluted with a linear gradient (−1.2 M/17 CV) of from 1.2 to 0 M ammonium sulfate. The HRase activity of each eluted fraction was measured, and fractions with the HRase activity were recovered and concentrated through a membrane.

Thereafter, this purification step using Phenyl Superose was performed once in an L-BH-free buffer system and then once in an L-BH-containing buffer system.

The enzyme solution obtained in the above procedures was used as purified HRase solution.

The increase in specific activity brought about by the above purification was measured. By measuring the HRase activity of both the cell-free extract after disruption of the microorganism and the active fraction obtained after purification, it was found that the specific activity per unit weight of the protein was increased 658-fold. In the activity measurement method described later, the specific activity of the purified HRase was estimated to be 79 U/mg.

The resulting active fraction was subjected in a usual manner to SDS-polyacrylamide gel electrophoresis and stained with Coomassie Brilliant Blue, and as a result it was confirmed that the HRase was purified to a single band, and its molecular weight was estimated to be 27,000. In consideration of the result of gel filtration, it was estimated that this HRase has a tetramer structure of subunits each having a molecular weight of 27,000.

7. Determination of an Amino Acid Sequence in the Vicinity of the N-Terminus

A sequence in the vicinity of the N-terminus of the HRase purified in the manner described above was determined in the following manner.

That is, about 10 µg protein out of the purified HRase fraction was subjected to polyacrylamide gel electrophoresis in the presence of SDS, and then the desired enzyme was transferred from the electrophoresed gel onto a polyvinylidene fluoride (PVDF (Bio-Rad, Trans-Blot)) membrane by use of a Milliblot (Millipore) in a semi-dry system ("Tanpakushitsu Kozo Kaiseki" (Structural Analysis of Protein) written by Hisashi Hirano, Tokyo Kagaku Dojin). Subsequently, the desired enzyme on the PVDF membrane was subjected to a protein sequencer (model 476A manufactured by ABI), to analyze its N-terminal amino acid sequence.

The amino acid sequence of 30 residues from the N-terminus was determined. The determined amino acid sequence in the vicinity of the N-terminus of HRase is set forth in SEQ ID NO:8 in the Sequence Listing.

Example 2

Effect of pH on HRase

The change (optimum pH) of the enzyme activity by reaction pH was determined in the following manner.

0.3 µg/ml purified HRase was used and reacted at 37° C. for 30 minutes in the presence of 0.1 M sodium acetate buffer (pH 3.1, 3.9, 4.9, 6.1), KPB (pH 6.4, 7.2, 8.0), or sodium carbonate buffer (pH 8.2, 9.1, 10.2, 10.9), to determine the reaction optimum pH of the HRase.

The measurement results were shown as relative enzyme activity against the actually measured pH of each reaction solution. For convenience sake, the highest activity was given 100. The measurement results are shown in FIG. 3.

Figure 3:
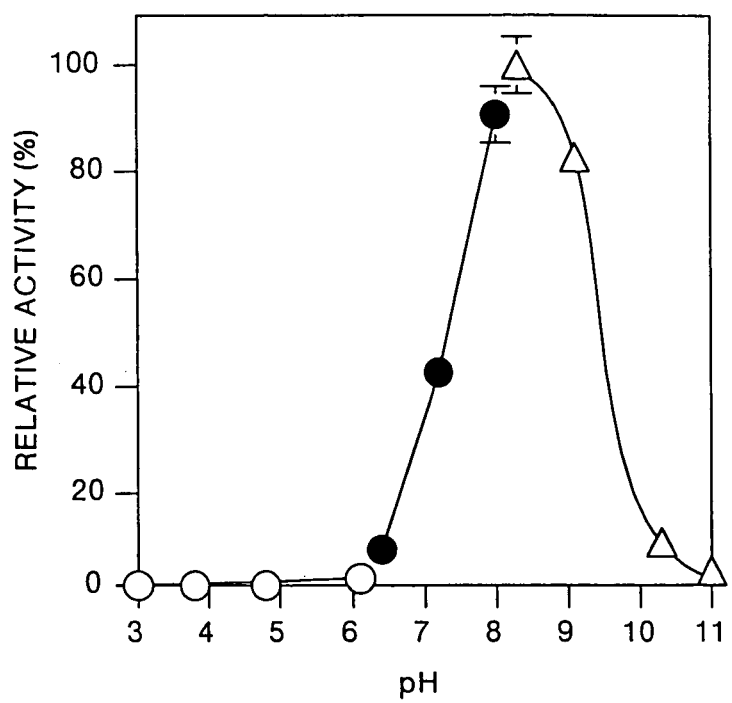
FIG. 3 is a drawing showing the optimum pH curve of the hydantoin racemase of the present invention.

The optimum pH of the HRase of the present invention is in the pH range of about 7 to about 9, strictly about pH 8.0 to 9.0 (see FIG. 3).

Example 3 pH Stability of HRase 3.0 μg/ml purified HRase was left at 0° C. for 30 minutes in the presence of 0.1 M buffer at each pH, and then adjusted to pH 8.0, and the enzyme was subjected to reaction at pH 8.0, at 37° C. for 30 minutes, and the residual activity was measured to determine the pH stability of the HRase.

The measurement results were shown as relative enzyme activity against pretreatment at each pH. For convenience sake, the highest activity was given 100. The measurement results are shown in FIG. 4.

Figure 4:
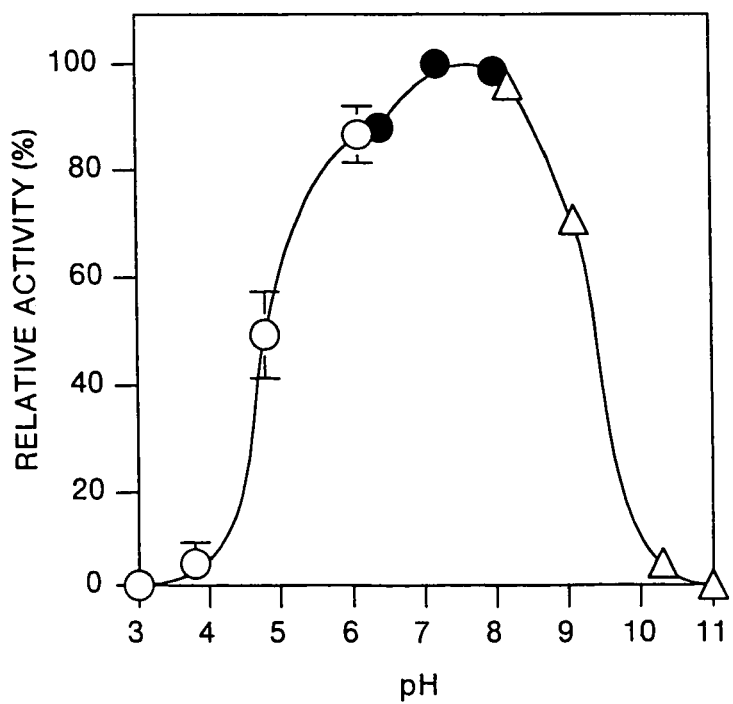
FIG. 4 is a drawing showing the pH stability curve of the hydantoin racemase of the present invention.

It was found that the HRase of the present invention is stable in the range of about pH 6 to 9 (see FIG. 4).

Example 4

Effect of Temperature on HRase 0.3 μg/ml purified HRase was used and reacted at pH 8.0 for 30 minutes at 0, 21, 30, 40, 50, 60, 70 and 80° C. respectively, to determine the working optimum temperature of the HRase.

Figure 5:
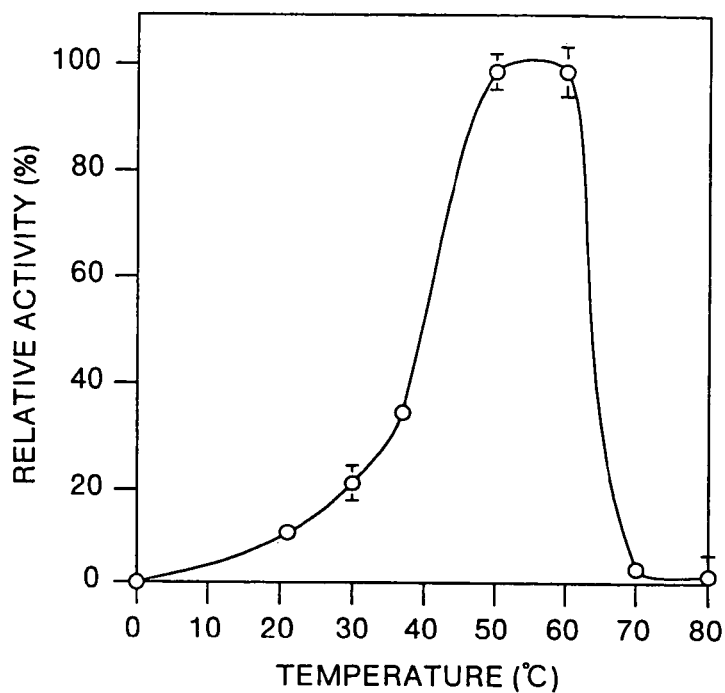
FIG. 5 is a drawing showing the optimum temperature curve of the hydantoin racemase of the present invention.

The measurement results were shown as relative enzyme activity against the actually measured temperature of each reaction solution. For convenience sake, the highest activity was given 100. The measurement results are shown in FIG. 5.

It was found that the optimum temperature of the HRase of the present invention is in the range of 50 to 60° C. (see FIG. 5). This optimum temperature in reaction is the highest among known HRases.

Example 5

Temperature Stability of HRase 3.0 μg/ml purified HRase was left at pH 8.0 for 30 minutes at 0, 21, 30, 40, 50, 60, 70 and 80° C., and then the enzyme was subjected to reaction at pH 8.0, at 37° C. for 30 minutes, and the residual activity was measured to determine the temperature stability of the HRase.

The measurement results were shown as relative enzyme activity against pretreatment at each temperature. For convenience sake, the highest activity was given 100. The measurement results are shown in FIG. 6.

Figure 6:
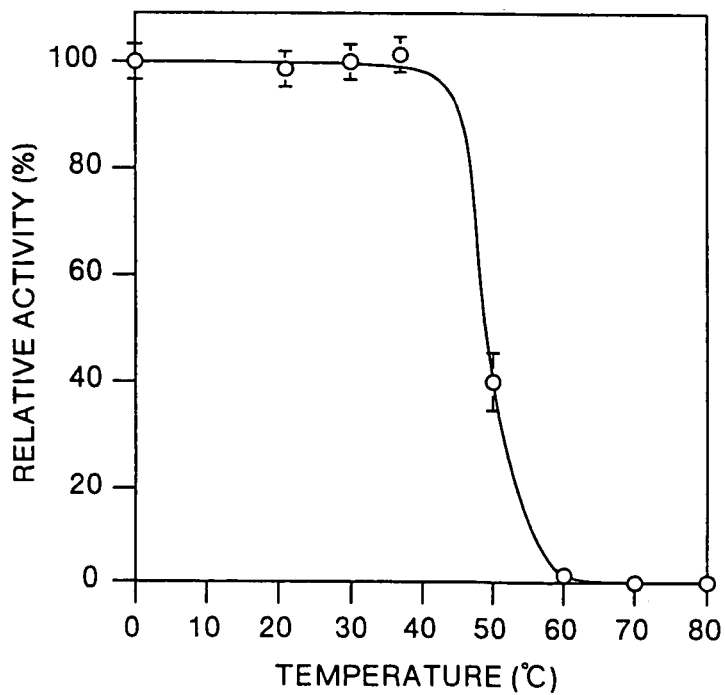
FIG. 6 is a drawing showing the temperature stability curve of the hydantoin racemase of the present invention.

It was found that the HRase of the present invention is stable in the range of 40° C. or less (see FIG. 6).

Example 6

Effect of Various Reagents such as Enzyme Inhibitors on HRase Activity 1.5 μg/ml purified HRase was pre-incubated at 0° C. for 30 minutes at pH 8.0 with 25 mM DTT, 25 mM N-ethyl-maleimide (NEM), 12.5 mM $CuSO_4$, 50 mM monoiodoacetic acid (IAA), 50 mM EDTA or 50% (v/v) methanol. As the enzyme source, each of these mixtures was reacted at pH 8.0, at 30° C. for 30 minutes to measure the residual activity, and the susceptibility of the HRase to each inhibitor was determined. The concentration of each of the enzyme and the inhibitor during the reaction was about ⅕ relative to the concentration during the pre-incubation.

The residual activity was shown as relative activity to the activity (100%) in the absence of the reagent (see Table 2). The HRase of the present invention was activated by DTT (not shown in the table) and significantly inhibited by a cysteine residue-modifying reagent such as NEM, iodoacetic acid or $Cu^{2+}$, suggesting the contribution of a cysteine residue to expression of the activity. Because no significant inhibitory effect was observed when EDTA was added, it was considered that no divalent ion is necessary for expression of the HRase activity. Further, pre-incubation with 50% (v/v) methanol did not influence the HRase activity (Table 2).

TABLE 2

| Reagent | Concentration | Residual Activity (%) |
|---------|---------------|----------------------|
| None | — | 100 |
| NEM | 5 mM | 0 |
| $CuSO_4$ | 2.5 mM | 0 |
| IAA | 10 mM | 0 |
| EDTA | 10 mM | 86 |
| Methanol | 10% (v/v) | 99 |

Example 7

Racemization of BH by Purified HRase

A reaction solution containing 0.3 mg/ml purified HRase, 0.12 g/dl D- or L-BH, 50 mM KPB (pH 8.0) and 5 mM DTT was incubated at 37° C. and sampled with time to quantify the amount of BH by HPLC. As the control, the same experiment was performed in an experimental group not containing the enzyme, to quantify the spontaneous racemization of BH. The results are shown in FIG. 7.

The HRase of the present invention recognized both D-BH and L-BH as substrates, and whichever substrate was used as the starting substrate, the reaction proceeded until the D, L-isomer ratio reached 1 : 1. However, the initial reaction rate of the racemization reaction was higher when L-BH was used as the starting substrate, and the specific activity of the purified HRase as calculated from the initial reaction rate was estimated to be 100 U/mg for formation of D-BH from L-BH and 79 U/mg for formation of L-BH from D-BH (see FIG. 7).

Figure 7:
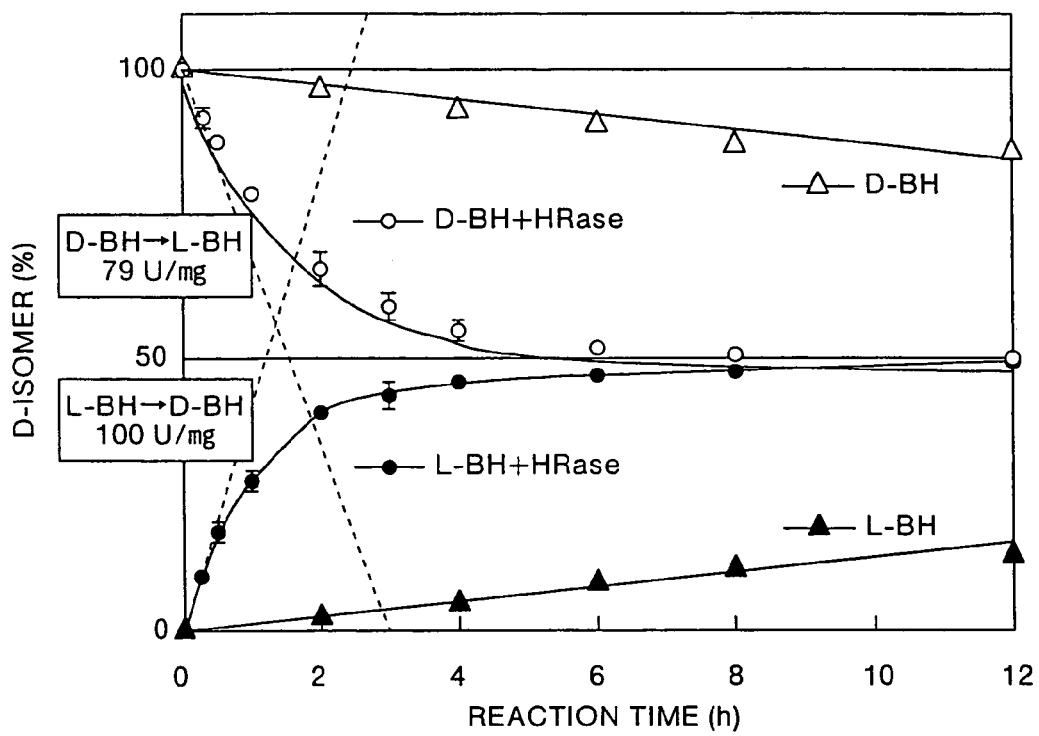
FIG. 7 is a drawing showing the time course of racemization of BH by the hydantoin racemase of the present invention. Where, ○: Substrate D-BH (HRase added), △: Substrate D-BH (HRase not added), ●: Substrate L-BH (HRase added), ▲: Substrate L-BH (HRase not added).

On the other hand, even in the control group where HRase was not added, spontaneous racemization of BH was observed, but the rate of this racemization was significantly low as compared with the rate of racemization catalyzed by HRase (see FIG. 7).

Example 8

Production of D-Phe from DL-BH or L-BH by a Combination of *Agrobacterium* sp. AJ11220 and HRase

*Agrobacterium* sp. AJ11220 is a microorganism deposited on Dec. 20, 1977 under FERM-P4347 with the National Institute of Bioscience and Human-Technology, the Agency of Industrial Science of Technology, the Ministry of International Trade and Industry. The microbial strain is known to hydrolyze a D-5-substituted hydantoin compound into its corresponding D-amino acid (Agric. Biol. Chem., 51, 721 (1987)). However, AJ11220 does not have any hydantoin racemase so that unless the hydantoin compound spontaneously racemizes, the L-5-substituted hydantoin compound not forming D-amino acid will remain, and therefore, the molar yield of D-amino acid formed from the DL-5-substituted hydantoin compounds that can be prepared inexpensively by chemical synthesis is 50% at the maximum. Accordingly, the production of D-Phe by a combination of the AJ11220 microorganism and the purified HRase was examined using the substrate BH that could hardly spontaneously racemize.

1. Culturing of AJ 11220 Strain

The microorganism was refreshed at 30° C. for 24 hours in GM2G agar medium (0.5 g/dl D-glucose, 1 g/dl yeast extract, 1 g/dl peptone, 0.5 g/dl NaCl, 2 g/dl agar, pH 7.0), followed by seed culture in GM2G liquid medium at 30° C. for 24 hours.

The main-culture medium used was prepared by autoclaving a medium consisting of 0.5 g/dl D-glucose, 0.5 g/dl $(NH_4)_2SO_4$, 1 g/dl yeast extract, 0.1 g/dl $KH_2PO_4$, 0.3 g/dl $K_2HPO_4$, 0.01 g/dl $MgSO_4.7H_2O$, pH 7.0, at 120° C. for 20 minutes and then adding 1 mg/dl each of $FeSO_4.7H_2O$ and $MnSO_4.4-5H_2O$ and 2 g/dl $CaCO_3$ thereto. 50 ml of this main-culture medium was introduced into a 500-ml Sakaguchi flask, and 1 ml of the seed culture liquid was inoculated thereinto and subjected to shake culture at 30° C. for 22 hours. For inducing the enzyme, D-glucose and DL-BH were added at final concentrations of 2 g/dl and 0.2 g/dl respectively in 14 hours after the main culture was initiated, and DL-BH was added at a final concentration of 0.2 g/dl in 16 and 18 hours after the main culture was initiated.

After the culture was finished, the microorganism was collected by centrifugation (10,000×g, 4° C., 10 minutes) and washed with 0.1 M KPB (pH 7.0), to give the washed microorganism.

2. Production of D-Phe form DL-BH or L-BH by a Combination of AJ 11220 and HRase 0.5 g/dl (26 mM) DL-BH or L-BH, together with 0.84 µg/ml purified HRase, 0.1 M KPB (pH 8.0), 0.5 mM $CoCl_2$ and 2 g/dl wet AJ11220 microorganism, was subjected to stationary reaction at 30° C. Oxygen was previously removed from the reaction solution by replacing it by nitrogen. The reaction solution was sampled with time and analyzed by HPLC to quantify the formed D-Phe.

Figure 8:
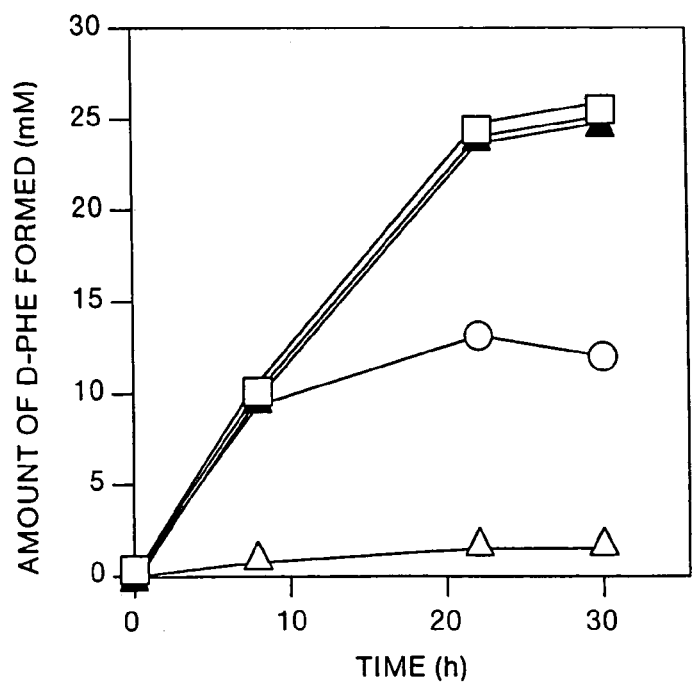
FIG. 8 is a drawing showing the time course of formation of D-Phe. Where, □: Substrate D-BH (HRase not added), ○: Substrate DL-BH (HRase not added), △: Substrate L-BH (HRase not added), ■: Substrate DL-BH (HRase added), ▲: Substrate L-BH (HRase added)

The time course of D-Phe formation is shown in FIG. 8. In the control where D-BH was used as the substrate in the absence of HRase, almost every substrate was converted into D-Phe in the reaction for 30 hours (amount of D-Phe produced, 25.4 mM and molar yield, 98% in □ in FIG. 8). On the other hand, the amount of D-Phe formed from DL-BH was 12.9 mM at the maximum (reaction, 22 hours and molar yield, 49% in ○ in FIG. 8), while the amount of D-Phe formed from L-BH was limited to 1.5 mM (reaction, 30 hours and molar yield, 6% in Δ in FIG. 8). The amount of D-Phe formed from DL-BH as the substrate was about half of the amount of D-Phe formed from D-BH as the substrate, and D-Phe was hardly formed from L-BH as the substrate, thus indicating that the rate-determining reaction of forming D-Phe from BH in this reaction system is the reaction of racemizing L-BH into D-BH.

When HRase was added, on the other hand, it was observed that in the reaction for 30 hours, 24.6 mM D-Phe (molar yield, 94%) (■ in FIG. 8) was formed from DL-BH, and 24.6 mM D-Phe (molar yield, 94%) (▲ in FIG. 8) was formed from L-BH. These values were almost equivalent to those achieved by using D-BH as the substrate, suggesting that the rate-determining reaction of racemizing L-BH into D-BH was almost completely resolved by adding HRase.

From the foregoing, when the DL- or L-5-substituted hydantoin compound is allowed to act in the D-isomer-selective hydrolysis reaction system to form its corresponding D-amino acid, in the case of 5-substituted hydantoin compound used as the substrate having no or less spontaneous racemization ability, the L-5-substituted hydantoin compound not undergoing hydrolysis will remain unreacted in the reaction solution; however, by combining the reaction system with HRase, the whole of the substrate can be efficiently hydrolyzed to form its corresponding D-amino acid in higher yield.

As a matter of course, when the 5-substituted hydantoin compound is allowed to act similarly in the L-isomer-selective hydrolysis reaction system to form its corresponding L-amino acid, the whole of the substrate can be efficiently hydrolyzed by combining the reaction system with HRase, whereby its corresponding L-amino acid can be formed in higher yield.

Example 9

Racemization of Various Optically Active 5-Substituted Hydantoin Compounds other than BH The ability of the present HRase to catalyze racemization of optically active 5-substituted hydantoin compounds other than BH was examined. The formation of D-amino acid from L-5-substituted hydantoin by a combination of *Pseudomonas* sp. AJ 11220 and HRase was confirmed in the same manner as in Example 8.

1 g/dl 5-substituted hydantoin of various kinds, together with 1.3 µg/ml purified HRase, 0.1 M KPB (pH 8.0), 0.5 mM $CoCl_2$ and 2 g/dl wet AJ 11220, was subjected to stationary reaction at 37° C. for 22 hours. Each hydantoin consisted of D- and L-isomers as the substrate, and it was confirmed that D-amino acid was formed from the D-isomer substrate in the absence of HRase, and also that D-amino acid was not formed from the L-isomer substrate in the absence of HRase, and then it was judged that when D-amino acid was formed from the L-isomer substrate in the presence of HRase, the substrate was recognized. The formation of D-amino acid was qualitatively estimated by development with optical resolution TLC (MERCK, HPTLC CHIR) with methanol: $H_2O$:acetonitrile=1:1:4.

As a result, it was recognized that HRase racemized L-5-indolyl methyl hydantoin, L-5-(p-hydroxybenzyl) hydantoin and L-5-isobutyl hydantoin to form their corresponding D-tryptophan, D-tyrosine and D-leucine respectively.

Example 10

Isolation of HRase Gene

Hereinafter, isolation of HRase gene and expression of HRase in *E. coli* are described where *Microbacterium liquefaciens* AJ3912 (FERM-P3133) was used as the bacterial strain. Isolation of the gene and expression of HRase were conducted using *E. coli* JM109 as the host and pUC18 as the vector.

1. Preparation of PCR Primers Based on the Determined Amino Acid Sequence

On the basis of the N-terminal amino acid sequence (SEQ ID NO:8 in the Sequence Listing) of HRase of *Microbacterium liquefaciens* AJ3912 (FERM-P3133), mix primers shown SEQ ID NOS:9 and 10 respectively were prepared.

2. Acquisition of the Microorganism

*Microbacterium liquefaciens* AJ3912 (FERM-P3133) was refreshed by culturing it at 30° C. for 24 hours in CM2G agar medium (0.5 g/dl glucose, 1.0 g/dl yeast extract, 1.0 g/dl peptone, 0.5 g/dl NaCl, 2 g/dl agar, pH 7.0). The microorganism was inoculated via one loop of platinum into a 500-ml Sakaguchi flask containing 50 ml CM2G liquid medium, and then cultured under shaking at 30° C. for 16 hours under aerobic conditions.

3. Acquisition of the Chromosomal DNA from the Microorganism 50 ml of the culture liquid was centrifuged (12,000×g, 4° C., 15 minutes), whereby the microorganism was collected. This microorganism was suspended in 10 ml of 50:20 TE (50 mM Tris-HCl, pH 8.0, 20 mM EDTA), washed and centrifuged, whereby the microorganism was recovered. This microorganism was suspended again in 10 ml of 50:20 TE. 0.5 ml of 20 mg/ml lysozyme solution and 1 ml of 10% SDS solution were added to the above suspension; followed by incubation at 55° C. for 20 minutes. After incubation, a 1-fold volume of 10:1 TE-saturated phenol was added thereto to remove proteins. A 1-fold volume of 2-propanol was added to the separated aqueous layer, to precipitate and recover DNA. After the precipitated DNA was dissolved in 0.5 ml of 50:20 TE, 5 µl of 10 mg/ml RNase and 5 µl of 10 mg/ml Proteinase K were added thereto and the mixture was reacted at 55° C. for 2 hours. After reaction, a 1-fold volume of 10:1 TE-saturated phenol was added thereto to remove proteins. Further, a 1-fold volume of 24:1 chloroform/isoamyl alcohol was added thereto and stirred, and the aqueous layer was recovered. This procedure was repeated further twice, and 3 M sodium acetate solution (pH 5.2) was added at a final concentration of 0.4 M to the resulting aqueous layer, followed by adding a 2-fold volume of ethanol thereto. The DNA occurring as precipitates was recovered, washed with 70% ethanol, dried and dissolved in 1 ml of 10:1 TE.

4. Acquisition of a DNA Fragment Containing a Part of the HRase Gene by the Cassette PCR Method For isolation and amplification of the DNA molecule containing the gene (fhr) coding for HRase by the cassette PCR method, TaKaRa LA PCR in vitro Cloning Kit (Takara Shuzo Co., Ltd) was used. Unless otherwise noted, the experiment was carried out according to instructions of the kit. In the cassette PCR method, when primer 1 (1st PCR) and primer 2 (2nd PCR) were used as the primers, an about 0.4-kb band (fragment 1) was amplified with HindIII cassette. By determining the nucleotide sequence of this fragment, fragment 1 was confirmed to be a part of fhr.

5. Cloning of the HRase Gene from a Gene Library

Then, Southern hybridization with fragment 1 as a probe was carried out to obtain the full-length fhr.

The concentration of the DNA fragment serving as a probe was adjusted to about 50 ng/µl, and 16 µl of this DNA solution was labeled as the probe by incubating it at 37° C. for 24 hours with DIG High Prime (Boehringer Mannheim)-according to its protocol.

1 µg chromosomal DNA was completely digested with a combination of various restriction enzymes, subjected to electrophoresis on 0.8% agarose gel, and blotted onto a nylon membrane (Boehringer Mannheim, Nylon membranes positively charged). Subsequently, Southern hybridization was conducted according to the conventional method. Hybridization was carried out using DIG Easy Hyb (Boehringer Mannheim), and after pre-hybridization at 50° C. for 30 minutes, the probe was added and hybridized at 50° C. for 18 hours. The sample was detected using a DIG Nucleotide Detection Kit (Boehringer Manheim).

As a result, a band was detected at a position of about 2.9 kb in the product cleaved with EcoRI/PstI.

This 2.9-kb fragment was recovered and ligated to pUC18, to prepare a library (120 strains) with *E. coli* JM109. Subsequently, colony hybridization was conducted according to the conventional method. The colonies were transferred onto a nylon membrane filter (Boehringer Mannheim, Nylon membranes for colony and plaque hybridization), followed by alkali denaturation, neutralization and immobilization. Hybridization was conducted using DIG Easy Hyb. The filter was immersed in a buffer and subjected to pre-hybridization at 42° C. for 30 minutes. Thereafter, the above-described labeled probe was added thereto and hybridized at 42° C. for 18 hours. After washing with SSC buffer, 1 positive clone strain was selected by using a DIG Nucleotide Detection Kit.

6. Nucleotide Sequence of the HRase Bene Derived from *Microbacterium liquefaciens* AJ3912 (FERM-P3133)

The plasmid maintained by the selected transformant was prepared by a method described in Molecular Cloning, 2nd edition, Cold Spring Harbor Press (1989), and a nucleotide sequence near to the sequence hybridized with the probe was determined. An open reading frame (ORF) coding for a protein containing the N-terminal amino acid sequence of 30 residues in HRase was present therein and confirmed to be the gene fhr coding for HRase. The nucleotide sequence of the full-length HRase gene is shown in SEQ ID NO:1 in the Sequence Listing. The resulting ORF showed 48% homology to known HRases (J. Bacteriol., 174, 962 (1992)) derived from microorganisms of the genus *Pseudomonas*.

7. Expression of HRase Gene in *E. coli*

To express fhr in *E. coli*, plasmid pUCFHR was constructed by ligating fhr to a downstream region of a lac promoter in pUC18. PCR was performed where the chromosomal DNA from *Microbacterium liquefaciens* AJ3912 (FERM-P3133) was used as the template and the oligonucleotides shown in Table 2 were used as the primers, and the amplified fragment was treated with EcoRI and BamHI and ligated to an EcoRI/BamHI-cleaved product of pUC18, and then transformed into *E. coli* JM109. From ampicillin resistant strains, a strain having the desired plasmid was selected, and the constructed plasmid was designated expression plasmid pUCFHR.

TABLE 3

| Primer | Sequence | |
|---|---|---|
| 5'-side | GCCGAATTCGCGACTGGCAACACGAAGG<br>EcoR I | SEQ ID NO:11 |
| 3'-side | CGGGGATCCTTCTCGTTAGAGGTACTGC<br>BamH I | SEQ ID NO:12 |

The HRase *E. coli* transformant harboring pUCFHR was subjected to seed culture at 37° C. for 16 hours in LB medium containing 0.1 mg/ml ampicillin. 1 ml of this pre-culture liquid was seeded in a 500-ml Sakaguchi flask containing 50 ml LB medium, and then cultured at 37° C. In 2.5 hours after culture was initiated, isopropyl-1-thio-β-D-galactopyranoside (IPTG) was add thereto at a final concentration of 1 mM, and culture was further continued for 4 hours.

After the culture was finished, the microorganism was collected, washed, suspended in 5 ml of 50 mM KPB (pH 8.0) and disrupted with 0.1 mmφ glass beads for 3 minutes (30 seconds×6 times at 90-second intervals) with a beads beater. The solution was recovered and centrifuged at 20,000 g×10 minutes, and the supernatant was used as the cell-free extract.

8. Measurement of HRase Activity

After the culture, the cell-free extract was prepared as an enzyme source and measured for its HRase activity.

For measurement of the HRase activity, a reaction solution containing 120 mg/dl L-BH, 50 mM KPB (pH 8.0), 5 mM DTT, 5 mM EDTA, 150 mM NaCl and the enzyme solution was incubated at 37° C. for 30 minutes, and the reaction was terminated by adding a 9-fold volume of 1.1 mM $CUSO_4$ and 11.1 mM $H_3PO_4$. By centrifugation at 20,000 g×10 minutes, precipitates were removed, and the amount of BH racemized was quantified by HPLC to determine the HRase activity. The enzyme activity causing racemization of 1 μmol BH per minute under these conditions was defined as 1 U of the enzyme activity.

The HPLC conditions used in analysis are as follows:
Column: Daicel Chemical CHIRALPAK WH 0.46 cmφ×25 cm
Mobile phase: 5% (v/v) methanol, 1 mM $CuSO_4$
Column temperature: 50° C.
Flow rate: 1.5 ml/min.
Detection: $UV_{210}$ As a result, the HRase activity was detected in only the *E. coli* having pUC18FHR introduced therein, and it was confirmed that the cloned fhr gene was expressed in *E. coli* (Table 4).

TABLE 4

Expression of HRase by *E. coli* having pUC18FHR introduced therein

| | Addition of IPTG | Protein concentration (mg/ml) in the cell-free extract | HRase activity (U/mg) |
|---|---|---|---|
| pUC18FHR | + | 1.9 | 0.15 |
| pUC18FHR | − | 3.4 | 0.06 |
| pUC18 | + | 2.2 | Not detected |
| pUC18 | − | 3.7 | Not detected |

According to the present invention, HRase not known so far can be obtained from a microorganism of the genus *Microbacterium*. As compared with HRases known in the art, this HRase is characterized by a higher optimum reaction temperature, so the reaction temperature can be increased, resulting in an increase in the reaction rate and efficient progress of the desired reaction. Further, the risk of contamination of the reaction solution with microorganisms during the reaction can be reduced and thus there is the advantage of easy process control including quality control. Further, by using the hydantoin racemase of the present invention in combination with a system of hydrolyzing 5-substituted hydantoin compounds optico-selectively, optically active amino acids useful for production pharmaceutical preparations, products in chemical industry, food additives can be formed in higher yield.

The present application claims priority to JP2000-278571 filed Sep. 13, 2000 and JP2001-65815 filed Mar. 8, 2001, the entire contents of both applications are incorporated herein by reference. obviously, numerous modifications and variations on the present invention are possible in light of the above teachings. It is therefore to be understood that within the scope of the appended claims, the invention may be practiced otherwise than as specifically described herein.

What is claimed is:

1. An isolated polypeptide comprising an amino acid sequence that is at least 95% identical to the polypeptide of SEQ ID NO:2.

2. A method of racemizing an optically active 5-substituted hydantoin compound, comprising contacting said 5-substituted hydantoin compound with the isolated polypeptide of claim 1.

3. The method of claim 2, wherein said contacting is performed in a culture comprising a microorganism expressing said polypeptide.

4. The method of claim 2, wherein said isolated polypeptide is in a cell lysis preparation.

5. The method of claim 2, wherein said 5-substituted hydantoin compound is at least one compound selected from the group consisting of 5-indolyl methyl hydantoin, 5-(p-hydroxybenzyl) hydantoin, 5-isobutyl hydantoin, and 5-(3'-pyridyl)-methyl hydantoin.

6. The isolated polypeptide, of claim 1, wherein said polypeptide has the amino acid sequence of SEQ ID NO:2.

7. A method of racemizing an optically active 5-substituted hydantoin compound, comprising contacting said 5-substituted hydantoin compound with the isolated polypeptide of claim 6.

8. The method of claim 7, wherein said contacting is performed in a culture comprising a microorganism expressing said polypeptide.

9. The method of claim 7, wherein said isolated polypeptide is in a cell lysis preparation.

10. The method of claim 7, wherein said 5-substituted hydantoin compound is at least one compound selected from the group consisting of 5-indolyl methyl hydantoin, 5-(p-hydroxybenzyl) hydantoin, 5-isobutyl hydantoin, and 5-(3'-pyridyl)-methyl hydantoin.

* * * * *

SEQUENCE LISTING

```
<160> NUMBER OF SEQ ID NOS: 12

<210> SEQ ID NO 1
<211> LENGTH: 711
<212> TYPE: DNA
<213> ORGANISM: Microbacterium liquefaciens
<220> FEATURE:
<221> NAME/KEY: CDS
<222> LOCATION: (1)..(708)
<223> OTHER INFORMATION:

<400> SEQUENCE: 1 atg aga atc cat gtc atc aat ccc aac agc tcg gtg gat ctc acc gat        48
Met Arg Ile His Val Ile Asn Pro Asn Ser Ser Val Asp Leu Thr Asp
1               5                   10                  15 gcg gtg gcc gag gcg gcg cga agt gtg gtg tca ccg gga acc acc atc        96
Ala Val Ala Glu Ala Ala Arg Ser Val Val Ser Pro Gly Thr Thr Ile
            20                  25                  30 acc gcg gtc aac cct tcg aag ggc ccc acg gtc atc gag ggc agt tac       144
Thr Ala Val Asn Pro Ser Lys Gly Pro Thr Val Ile Glu Gly Ser Tyr
        35                  40                  45 gac gag gtg ctg gcc acg tat cac ctc gtc gaa gag gtc cgc cgc gcg       192
Asp Glu Val Leu Ala Thr Tyr His Leu Val Glu Glu Val Arg Arg Ala
```

```
                    50                     55                     60
gag cgc gaa gac cga ccg gac gcc tac gtc atc gcc tgt ttc ggc gat    240
Glu Arg Glu Asp Arg Pro Asp Ala Tyr Val Ile Ala Cys Phe Gly Asp
 65                  70                     75                  80 cca ggt ctc gac gcc gtc agg gag ctc acc gac agg ccc gtg gtc gga    288
Pro Gly Leu Asp Ala Val Arg Glu Leu Thr Asp Arg Pro Val Val Gly
                 85                     90                     95 atc gcc gag gcg gcg atc cag atg acg agc ttc gtc gcc gcg agc ttc    336
Ile Ala Glu Ala Ala Ile Gln Met Thr Ser Phe Val Ala Ala Ser Phe
                100                    105                    110 tcc atc gtg agc atc ctc ccg cgc gtg cgc aag cat ctg cac gag ctg    384
Ser Ile Val Ser Ile Leu Pro Arg Val Arg Lys His Leu His Glu Leu
            115                    120                    125 gtg cac cgg gcg ggg gca acg gat cga ctc gcc tca ctc aag ctt ccg    432
Val His Arg Ala Gly Ala Thr Asp Arg Leu Ala Ser Leu Lys Leu Pro
        130                    135                    140 gat ctc gga gtg ctc gca ttc cac gag gac gag gca gcg gcg ttc gag    480
Asp Leu Gly Val Leu Ala Phe His Glu Asp Glu Ala Ala Ala Phe Glu
145                    150                    155                    160 acc ctc cgg cgc gtg gca ggt gag gcg gtg cgc gag gac ggc gcg gag    528
Thr Leu Arg Arg Val Ala Gly Glu Ala Val Arg Glu Asp Gly Ala Glu
                165                    170                    175 tcg atc gtg ctc ggc tgc gcg ggc atg gcc gga ttc gcc aga cag ctg    576
Ser Ile Val Leu Gly Cys Ala Gly Met Ala Gly Phe Ala Arg Gln Leu
            180                    185                    190 agt gaa gag ctc ggc gtc ccc gtc atc gac gcg gtc gag gca gcc tgc    624
Ser Glu Glu Leu Gly Val Pro Val Ile Asp Ala Val Glu Ala Ala Cys
        195                    200                    205 cgc gtc gcg gag agc ctc gtc gcc ctg ggg tac cgc acc agc aag gcg    672
Arg Val Ala Glu Ser Leu Val Ala Leu Gly Tyr Arg Thr Ser Lys Ala
    210                    215                    220 aac acc tac caa gca ccc acc gag aag cag tac ctc taa                711
Asn Thr Tyr Gln Ala Pro Thr Glu Lys Gln Tyr Leu
225                    230                    235

<210> SEQ ID NO 2
<211> LENGTH: 236
<212> TYPE: PRT
<213> ORGANISM: Microbacterium liquefaciens

<400> SEQUENCE: 2

Met Arg Ile His Val Ile Asn Pro Asn Ser Val Asp Leu Thr Asp
1               5                   10                  15

Ala Val Ala Glu Ala Ala Arg Ser Val Val Ser Pro Gly Thr Thr Ile
                20                  25                  30

Thr Ala Val Asn Pro Ser Lys Gly Pro Thr Val Ile Glu Gly Ser Tyr
            35                  40                  45

Asp Glu Val Leu Ala Thr Tyr His Leu Val Glu Glu Val Arg Arg Ala
        50                  55                  60

Glu Arg Glu Asp Arg Pro Asp Ala Tyr Val Ile Ala Cys Phe Gly Asp
65                  70                  75                  80

Pro Gly Leu Asp Ala Val Arg Glu Leu Thr Asp Arg Pro Val Val Gly
                85                  90                  95

Ile Ala Glu Ala Ala Ile Gln Met Thr Ser Phe Val Ala Ala Ser Phe
            100                 105                 110

Ser Ile Val Ser Ile Leu Pro Arg Val Arg Lys His Leu His Glu Leu
        115                 120                 125

Val His Arg Ala Gly Ala Thr Asp Arg Leu Ala Ser Leu Lys Leu Pro
```

-continued

```
                  130                 135                 140
Asp Leu Gly Val Leu Ala Phe His Glu Asp Glu Ala Ala Phe Glu
145                 150                 155                 160

Thr Leu Arg Arg Val Ala Gly Glu Ala Val Arg Glu Asp Gly Ala Glu
                165                 170                 175

Ser Ile Val Leu Gly Cys Ala Gly Met Ala Gly Phe Ala Arg Gln Leu
                180                 185                 190

Ser Glu Glu Leu Gly Val Pro Val Ile Asp Ala Val Glu Ala Ala Cys
            195                 200                 205

Arg Val Ala Glu Ser Leu Val Ala Leu Gly Tyr Arg Thr Ser Lys Ala
        210                 215                 220

Asn Thr Tyr Gln Ala Pro Thr Glu Lys Gln Tyr Leu
225                 230                 235

<210> SEQ ID NO 3
<211> LENGTH: 1380
<212> TYPE: DNA
<213> ORGANISM: Microbacterium liquefaciens
<220> FEATURE:
<221> NAME/KEY: CDS
<222> LOCATION: (1)..(1377)
<223> OTHER INFORMATION:

<400> SEQUENCE: 3 atg ttc gac gtc att gtg aag aac tgt cga gtg gtt tcc agt cag ggc        48
Met Phe Asp Val Ile Val Lys Asn Cys Arg Val Val Ser Ser Gln Gly
1               5                   10                  15 atc atc gaa gcc gac atc ctc gtg aag gac ggc cgg atc gcc gcc atc        96
Ile Ile Glu Ala Asp Ile Leu Val Lys Asp Gly Arg Ile Ala Ala Ile
            20                  25                  30 agc gag gag ccc ctc gag gcc gaa gcc gcc cgg acc atc gat gcc gca       144
Ser Glu Glu Pro Leu Glu Ala Glu Ala Ala Arg Thr Ile Asp Ala Ala
        35                  40                  45 ggc agg ttc gtg atg ccc ggt gtg gtc gat gaa cac gtg cac atc atc       192
Gly Arg Phe Val Met Pro Gly Val Val Asp Glu His Val His Ile Ile
    50                  55                  60 gac atg gat ctg aag gag gtc tac ggg cgg ttc gaa ctc gat tcc gag       240
Asp Met Asp Leu Lys Glu Val Tyr Gly Arg Phe Glu Leu Asp Ser Glu
65                  70                  75                  80 tcg gcg gcc gtc ggc ggt gtg acc acc atc atc gag atg ccg atc acg       288
Ser Ala Ala Val Gly Gly Val Thr Thr Ile Ile Glu Met Pro Ile Thr
                85                  90                  95 ttc ccg ccc acg acc acc ctg gag gcc ttc ctc gag aag aag aag cag       336
Phe Pro Pro Thr Thr Thr Leu Glu Ala Phe Leu Glu Lys Lys Lys Gln
            100                 105                 110 gga gag cag cga ctc aag gtc gac ttc gcg ctg tac ggc ggc gga gtg       384
Gly Glu Gln Arg Leu Lys Val Asp Phe Ala Leu Tyr Gly Gly Gly Val
        115                 120                 125 ccc gga aac ctg agc gag atc cgg aag atg cat gat gcc ggc gcc gtg       432
Pro Gly Asn Leu Ser Glu Ile Arg Lys Met His Asp Ala Gly Ala Val
    130                 135                 140 ggc ttc aag tcg atg atg gcg gcc tcc gtt ccc ggg atg ttc gaa gcc       480
Gly Phe Lys Ser Met Met Ala Ala Ser Val Pro Gly Met Phe Glu Ala
145                 150                 155                 160 gtc gac gac gga cag ctg ttc gag atc ttc cag gag atc gcg gcc tgc       528
Val Asp Asp Gly Gln Leu Phe Glu Ile Phe Gln Glu Ile Ala Ala Cys
                165                 170                 175 ggc tcg gtg atc gtg gtg cac gcc gag aac gag atg ctc atc cag acg       576
Gly Ser Val Ile Val Val His Ala Glu Asn Glu Met Leu Ile Gln Thr
            180                 185                 190
```

```
ctg cag aag cag ctc aag gcg gcc ggg cgc aag gac ctg gcg gcg tat        624
Leu Gln Lys Gln Leu Lys Ala Ala Gly Arg Lys Asp Leu Ala Ala Tyr
        195                 200                 205 gag gcg tcc cag ccg gtc ttc cag gag aac gag gcg atc cag cgc gcg        672
Glu Ala Ser Gln Pro Val Phe Gln Glu Asn Glu Ala Ile Gln Arg Ala
    210                 215                 220 ctg ctc ctg cag aag gag gcg ggc tgc cga ctc atc gtc gtt cac gtg        720
Leu Leu Leu Gln Lys Glu Ala Gly Cys Arg Leu Ile Val Val His Val
225                 230                 235                 240 agc aac ccc ggc ggc gtg gag ttg atc cac aag gcg cag tcg gag ggt        768
Ser Asn Pro Gly Gly Val Glu Leu Ile His Lys Ala Gln Ser Glu Gly
                245                 250                 255 cag gac gtg cac tgc gag tca ggc cct cag tac ctc aac ctc aca atg        816
Gln Asp Val His Cys Glu Ser Gly Pro Gln Tyr Leu Asn Leu Thr Met
            260                 265                 270 gat gac gcc gag aag gtc ggc ccg tac atg aag atc gcc ccg ccg gtc        864
Asp Asp Ala Glu Lys Val Gly Pro Tyr Met Lys Ile Ala Pro Pro Val
        275                 280                 285 cgt tcg gcc gag ctg aac gcc gtc ctc tgg gag cag ctc gag aag ggg        912
Arg Ser Ala Glu Leu Asn Ala Val Leu Trp Glu Gln Leu Glu Lys Gly
    290                 295                 300 tac atc gac acg ctc gga tcg gat cac ggt ggg cac ccc gtc gag aac        960
Tyr Ile Asp Thr Leu Gly Ser Asp His Gly Gly His Pro Val Glu Asn
305                 310                 315                 320 aag gag ggc ggc tgg gac gac atc tgg acg gcc agc aac ggt gcg ctg       1008
Lys Glu Gly Gly Trp Asp Asp Ile Trp Thr Ala Ser Asn Gly Ala Leu
                325                 330                 335 gga ctg gag acg tcg ctg ccg atg atg ctg acc aac ggc gtc aac aag       1056
Gly Leu Glu Thr Ser Leu Pro Met Met Leu Thr Asn Gly Val Asn Lys
            340                 345                 350 ggc cgc gtc tcg ctg gag cga ctg gtc gag gtg atg tgc gag aac ccg       1104
Gly Arg Val Ser Leu Glu Arg Leu Val Glu Val Met Cys Glu Asn Pro
        355                 360                 365 gcg aag ctc ttc ggg atc tat ccg cag aag ggc acg ctc cag gtc ggc       1152
Ala Lys Leu Phe Gly Ile Tyr Pro Gln Lys Gly Thr Leu Gln Val Gly
    370                 375                 380 tcg gac gcc gat ctc ctc atc ctc gat ctc gag atc gag gac agg aag       1200
Ser Asp Ala Asp Leu Leu Ile Leu Asp Leu Glu Ile Glu Asp Arg Lys
385                 390                 395                 400 gtg gat gct tcg cag ttc cgc tcg ctc ctg cac tac agt cca ttc gat       1248
Val Asp Ala Ser Gln Phe Arg Ser Leu Leu His Tyr Ser Pro Phe Asp
                405                 410                 415 gga cgg ccg gtc acc ggc gcg ccc gtc ctc acg atg atc cgt gga aca       1296
Gly Arg Pro Val Thr Gly Ala Pro Val Leu Thr Met Ile Arg Gly Thr
            420                 425                 430 gtc gtc gcc cag gac gga gag atc ctc gtc gac cag ggg ttc ggg cag       1344
Val Val Ala Gln Asp Gly Glu Ile Leu Val Asp Gln Gly Phe Gly Gln
        435                 440                 445 ttc gtg acc cgg cgc gac agc gag gtg tcg tcg tga                       1380
Phe Val Thr Arg Arg Asp Ser Glu Val Ser Ser
    450                 455

<210> SEQ ID NO 4
<211> LENGTH: 459
<212> TYPE: PRT
<213> ORGANISM: Microbacterium liquefaciens

<400> SEQUENCE: 4

Met Phe Asp Val Ile Val Lys Asn Cys Arg Val Val Ser Ser Gln Gly
1               5                   10                  15
```

-continued

```
Ile Ile Glu Ala Asp Ile Leu Val Lys Asp Gly Arg Ile Ala Ala Ile
             20                  25                  30

Ser Glu Glu Pro Leu Glu Ala Glu Ala Ala Arg Thr Ile Asp Ala Ala
             35                  40                  45

Gly Arg Phe Val Met Pro Gly Val Val Asp Glu His Val His Ile Ile
             50                  55                  60

Asp Met Asp Leu Lys Glu Val Tyr Gly Arg Phe Glu Leu Asp Ser Glu
 65                  70                  75                  80

Ser Ala Ala Val Gly Gly Val Thr Thr Ile Ile Glu Met Pro Ile Thr
                     85                  90                  95

Phe Pro Pro Thr Thr Thr Leu Glu Ala Phe Leu Glu Lys Lys Lys Gln
                100                 105                 110

Gly Glu Gln Arg Leu Lys Val Asp Phe Ala Leu Tyr Gly Gly Gly Val
                115                 120                 125

Pro Gly Asn Leu Ser Glu Ile Arg Lys Met His Asp Ala Gly Ala Val
                130                 135                 140

Gly Phe Lys Ser Met Met Ala Ala Ser Val Pro Gly Met Phe Glu Ala
145                 150                 155                 160

Val Asp Asp Gly Gln Leu Phe Glu Ile Phe Gln Glu Ile Ala Ala Cys
                165                 170                 175

Gly Ser Val Ile Val Val His Ala Glu Asn Glu Met Leu Ile Gln Thr
                180                 185                 190

Leu Gln Lys Gln Leu Lys Ala Ala Gly Arg Lys Asp Leu Ala Ala Tyr
                195                 200                 205

Glu Ala Ser Gln Pro Val Phe Gln Glu Asn Glu Ala Ile Gln Arg Ala
                210                 215                 220

Leu Leu Leu Gln Lys Glu Ala Gly Cys Arg Leu Ile Val Val His Val
225                 230                 235                 240

Ser Asn Pro Gly Gly Val Glu Leu Ile His Lys Ala Gln Ser Glu Gly
                245                 250                 255

Gln Asp Val His Cys Glu Ser Gly Pro Gln Tyr Leu Asn Leu Thr Met
                260                 265                 270

Asp Asp Ala Glu Lys Val Gly Pro Tyr Met Lys Ile Ala Pro Pro Val
                275                 280                 285

Arg Ser Ala Glu Leu Asn Ala Val Leu Trp Glu Gln Leu Glu Lys Gly
                290                 295                 300

Tyr Ile Asp Thr Leu Gly Ser Asp His Gly His Pro Val Glu Asn
305                 310                 315                 320

Lys Glu Gly Gly Trp Asp Asp Ile Trp Thr Ala Ser Asn Gly Ala Leu
                325                 330                 335

Gly Leu Glu Thr Ser Leu Pro Met Met Leu Thr Asn Gly Val Asn Lys
                340                 345                 350

Gly Arg Val Ser Leu Glu Arg Leu Val Glu Val Met Cys Glu Asn Pro
                355                 360                 365

Ala Lys Leu Phe Gly Ile Tyr Pro Gln Lys Gly Thr Leu Gln Val Gly
                370                 375                 380

Ser Asp Ala Asp Leu Leu Ile Leu Asp Leu Glu Ile Glu Asp Arg Lys
385                 390                 395                 400

Val Asp Ala Ser Gln Phe Arg Ser Leu Leu His Tyr Ser Pro Phe Asp
                405                 410                 415

Gly Arg Pro Val Thr Gly Ala Pro Val Leu Thr Met Ile Arg Gly Thr
                420                 425                 430
```

-continued

```
Val Val Ala Gln Asp Gly Glu Ile Leu Val Asp Gln Gly Phe Gly Gln
        435                 440                 445

Phe Val Thr Arg Arg Asp Ser Glu Val Ser Ser
    450                 455

<210> SEQ ID NO 5
<211> LENGTH: 1239
<212> TYPE: DNA
<213> ORGANISM: Microbacterium liquefaciens
<220> FEATURE:
<221> NAME/KEY: CDS
<222> LOCATION: (1)..(1236)
<223> OTHER INFORMATION:

<400> SEQUENCE: 5 gtg acg ctg cag cag gcg cgg gcc gat cgc atc gag gag gag ctc tgg      48
Val Thr Leu Gln Gln Ala Arg Ala Asp Arg Ile Glu Glu Glu Leu Trp
1               5                   10                  15 act ctc tcc cgc ttc tcg gtc gaa ggg ccc ggc gtg aca cgt ctc acg      96
Thr Leu Ser Arg Phe Ser Val Glu Gly Pro Gly Val Thr Arg Leu Thr
            20                  25                  30 tac act ccg gag cac gcc gcc gcg cga gag gtg atc gtc gcc gcc atg     144
Tyr Thr Pro Glu His Ala Ala Ala Arg Glu Val Ile Val Ala Ala Met
        35                  40                  45 cag cgg acg ggg ctg agc gtc cac gag gac gct ctc ggc aac atc atc     192
Gln Arg Thr Gly Leu Ser Val His Glu Asp Ala Leu Gly Asn Ile Ile
    50                  55                  60 ggt cgg cgt gag ggg agc gac ccc gct ctg ccg gcg atc gcc ttc ggc     240
Gly Arg Arg Glu Gly Ser Asp Pro Ala Leu Pro Ala Ile Ala Phe Gly
65                  70                  75                  80 tcg cac ttc gac tcg gtc cgc aac ggc ggg atg ttc gac ggc acc gcg     288
Ser His Phe Asp Ser Val Arg Asn Gly Gly Met Phe Asp Gly Thr Ala
                85                  90                  95 ggc gtg gtg tgc gcg ctc gag gct gcg agg gtg ctg cag gag agc gga     336
Gly Val Val Cys Ala Leu Glu Ala Ala Arg Val Leu Gln Glu Ser Gly
            100                 105                 110 tat gtg aac cgt cat cct ctc gag gtc atc gcg atc gtc gaa gag gag     384
Tyr Val Asn Arg His Pro Leu Glu Val Ile Ala Ile Val Glu Glu Glu
        115                 120                 125 ggc acc cgc ttc agc agc ggc atg ctg ggc ggt cgc gcg atc gcg ggg     432
Gly Thr Arg Phe Ser Ser Gly Met Leu Gly Gly Arg Ala Ile Ala Gly
    130                 135                 140 ctc gtg tcc gac gcc gat ctg gac acc ctg gtg gac gaa gac ggc gtg     480
Leu Val Ser Asp Ala Asp Leu Asp Thr Leu Val Asp Glu Asp Gly Val
145                 150                 155                 160 acg gtg cgc gag gcg gcc acg gcc ttc ggg ctg gaa ccg ggt gag ctg     528
Thr Val Arg Glu Ala Ala Thr Ala Phe Gly Leu Glu Pro Gly Glu Leu
                165                 170                 175 cgg acg gcg gcc cgt acg agg gat gac ctt cgc gcc ttc atc gag ttg     576
Arg Thr Ala Ala Arg Thr Arg Asp Asp Leu Arg Ala Phe Ile Glu Leu
            180                 185                 190 cac atc gag cag ggg ccg atc ctc gag cag gag aag gtg gag atc ggc     624
His Ile Glu Gln Gly Pro Ile Leu Glu Gln Glu Lys Val Glu Ile Gly
        195                 200                 205 gtc gtg acg ggg atc gtc ggt gtc cgc gcc ttc cgg atc acg gtg gag     672
Val Val Thr Gly Ile Val Gly Val Arg Ala Phe Arg Ile Thr Val Glu
    210                 215                 220 ggc agg agc gac cac gcc ggg acg acc ccc atg cac ctg cgg cag gac     720
Gly Arg Ser Asp His Ala Gly Thr Thr Pro Met His Leu Arg Gln Asp
225                 230                 235                 240 gcg ctg gtg ccg gcg gcg ctc atg gtg cga gag atc aat cgg ttc gtc     768
Ala Leu Val Pro Ala Ala Leu Met Val Arg Glu Ile Asn Arg Phe Val
```

```
Ala Leu Val Pro Ala Leu Met Val Arg Glu Ile Asn Arg Phe Val
            245                 250                 255 aac gag atc gcg gac ggc acg gtg gcg acc gtc ggc cac ctc acg gtg       816
Asn Glu Ile Ala Asp Gly Thr Val Ala Thr Val Gly His Leu Thr Val
            260                 265                 270 acc cct ggt ggg ctc aac cag gtt ccc ggg ggc gtc gag ttc acg ctc       864
Thr Pro Gly Gly Leu Asn Gln Val Pro Gly Gly Val Glu Phe Thr Leu
        275                 280                 285 gat ctg cga tcg ccc cac gag gag tcg atc cgg ctc ctg gtc gac agg       912
Asp Leu Arg Ser Pro His Glu Glu Ser Ile Arg Leu Leu Val Asp Arg
        290                 295                 300 atc gag gcg atg gtg gca gaa gtc gcc gcc gcg gcc gga gtc gag gcc       960
Ile Glu Ala Met Val Ala Glu Val Ala Ala Ala Ala Gly Val Glu Ala
305                 310                 315                 320 gcg gtg aac ggg ttc ttc gcg ctc agc cct gtc ggt ctg tct ccg gtg      1008
Ala Val Asn Gly Phe Phe Ala Leu Ser Pro Val Gly Leu Ser Pro Val
                325                 330                 335 gtc gtg gat cgc gtg cgc gac gcg gcg tcc gaa ctc ggc ttc acc cat      1056
Val Val Asp Arg Val Arg Asp Ala Ala Ser Glu Leu Gly Phe Thr His
            340                 345                 350 cgc gac atc acg agc ggg gca ggg cac gac tcg atg ttc atc gcc cag      1104
Arg Asp Ile Thr Ser Gly Ala Gly His Asp Ser Met Phe Ile Ala Gln
        355                 360                 365 atc acc gac gtc gga atg gtg ttc gtc ccc agc cgc gcc ggg cga agc      1152
Ile Thr Asp Val Gly Met Val Phe Val Pro Ser Arg Ala Gly Arg Ser
370                 375                 380 cat gtg ccg gag gaa tgg tcc gat ttc gac gat ctg cgg aag ggg acg      1200
His Val Pro Glu Glu Trp Ser Asp Phe Asp Asp Leu Arg Lys Gly Thr
385                 390                 395                 400 gat gtg gtc ctt cac gtc gtg acg gcg ctt gac cgg tga                  1239
Asp Val Val Leu His Val Val Thr Ala Leu Asp Arg
                405                 410

<210> SEQ ID NO 6
<211> LENGTH: 412
<212> TYPE: PRT
<213> ORGANISM: Microbacterium liquefaciens

<400> SEQUENCE: 6

Val Thr Leu Gln Gln Ala Arg Ala Asp Arg Ile Glu Glu Leu Trp
1               5                   10                  15

Thr Leu Ser Arg Phe Ser Val Glu Gly Pro Gly Val Thr Arg Leu Thr
            20                  25                  30

Tyr Thr Pro Glu His Ala Ala Ala Arg Glu Val Ile Val Ala Ala Met
        35                  40                  45

Gln Arg Thr Gly Leu Ser Val His Glu Asp Ala Leu Gly Asn Ile Ile
    50                  55                  60

Gly Arg Arg Glu Gly Ser Asp Pro Ala Leu Pro Ala Ile Ala Phe Gly
65                  70                  75                  80

Ser His Phe Asp Ser Val Arg Asn Gly Gly Met Phe Asp Gly Thr Ala
                85                  90                  95

Gly Val Val Cys Ala Leu Glu Ala Ala Arg Val Leu Gln Glu Ser Gly
            100                 105                 110

Tyr Val Asn Arg His Pro Leu Glu Val Ile Ala Ile Val Glu Glu Glu
        115                 120                 125

Gly Thr Arg Phe Ser Ser Gly Met Leu Gly Gly Arg Ala Ile Ala Gly
    130                 135                 140

Leu Val Ser Asp Ala Asp Leu Asp Thr Leu Val Asp Glu Asp Gly Val
```

```
                145                 150                 155                 160
Thr Val Arg Glu Ala Ala Thr Ala Phe Gly Leu Glu Pro Gly Glu Leu
                    165                 170                 175
Arg Thr Ala Ala Arg Thr Arg Asp Asp Leu Arg Ala Phe Ile Glu Leu
                180                 185                 190
His Ile Glu Gln Gly Pro Ile Leu Glu Gln Glu Lys Val Glu Ile Gly
                195                 200                 205
Val Val Thr Gly Ile Val Gly Val Arg Ala Phe Arg Ile Thr Val Glu
            210                 215                 220
Gly Arg Ser Asp His Ala Gly Thr Thr Pro Met His Leu Arg Gln Asp
225                 230                 235                 240
Ala Leu Val Pro Ala Ala Leu Met Val Arg Glu Ile Asn Arg Phe Val
                245                 250                 255
Asn Glu Ile Ala Asp Gly Thr Val Ala Thr Val Gly His Leu Thr Val
                260                 265                 270
Thr Pro Gly Gly Leu Asn Gln Val Pro Gly Gly Val Glu Phe Thr Leu
            275                 280                 285
Asp Leu Arg Ser Pro His Glu Glu Ser Ile Arg Leu Leu Val Asp Arg
            290                 295                 300
Ile Glu Ala Met Val Ala Glu Val Ala Ala Ala Gly Val Glu Ala
305                 310                 315                 320
Ala Val Asn Gly Phe Phe Ala Leu Ser Pro Val Gly Leu Ser Pro Val
                325                 330                 335
Val Val Asp Arg Val Arg Asp Ala Ala Ser Glu Leu Gly Phe Thr His
            340                 345                 350
Arg Asp Ile Thr Ser Gly Ala Gly His Asp Ser Met Phe Ile Ala Gln
            355                 360                 365
Ile Thr Asp Val Gly Met Val Phe Val Pro Ser Arg Ala Gly Arg Ser
        370                 375                 380
His Val Pro Glu Glu Trp Ser Asp Phe Asp Asp Leu Arg Lys Gly Thr
385                 390                 395                 400
Asp Val Val Leu His Val Val Thr Ala Leu Asp Arg
                405                 410

<210> SEQ ID NO 7
<211> LENGTH: 3343
<212> TYPE: DNA
<213> ORGANISM: Microbacterium liquefaciens

<400> SEQUENCE: 7
atgagaatcc atgtcatcaa tcccaacagc tcggtggatc tcaccgatgc ggtggccgag     60
gcggcgcgaa gtgtggtgtc accgggaacc accatcaccg cggtcaaccc ttcgaagggc    120
cccacggtca tcgagggcag ttacgacgag gtgctggcca cgtatcacct cgtcgaagag    180
gtccgccgcg cggagcgcga agaccgaccg gacgcctacg tcatcgcctg tttcggcgat    240
ccaggtctcg acgccgtcag ggagctcacc gacaggcccg tggtcggaat cgccgaggcg    300
gcgatccaga tgacgagctt cgtcgccgcg agcttctcca tcgtgagcat cctcccgcgc    360
gtgcgcaagc atcctgcacga gctggtgcac cgggcggggg caacggatcg actcgcctca    420
ctcaagcttc cggatctcgg agtgctcgca ttccacgagg acgaggcagc ggcgttcgag    480
accctccggc gcgtggcagg tgaggcggtg cgcgaggacg cgcggagtc gatcgtgctc    540 ggctgcgcgg gcatggccgg attcgccaga cagctgagtg aagagctcgg cgtccccgtc    600
atcgacgcgg tcgaggcagc ctgccgcgtc gcggagagcc tcgtcgccct ggggtaccgc    660
```

-continued

```
accagcaagg cgaacaccta ccaagcaccc accgagaagc agtacctcta acgagaagga       720
gcgatgtcat gttcgacgtc attgtgaaga actgtcgagt ggtttccagt cagggcatca       780
tcgaagccga catcctcgtg aaggacggcc ggatcgccgc catcagcgag gagcccctcg       840
aggccgaagc cgcccggacc atcgatgccg caggcaggtt cgtgatgccc ggtgtggtcg       900
atgaacacgt gcacatcatc gacatggatc tgaaggaggt ctacgggcgg ttcgaactcg       960
attccgagtc ggcggccgtc ggcggtgtga ccaccatcat cgagatgccg atcacgttcc      1020
cgcccacgac caccctggag gccttcctcg agaagaagaa gcaggagag cagcgactca       1080 aggtcgactt cgcgctgtac ggcggcggag tgcccggaaa cctgagcgag atccggaaga      1140
tgcatgatgc cggcgccgtg ggcttcaagt cgatgatggc ggcctccgtt cccgggatgt      1200
tcgaagccgt cgacgacgga cagctgttcg agatcttcca ggagatcgcg gcctgcggct      1260
cggtgatcgt ggtgcacgcc gagaacgaga tgctcatcca cacgctgcag aagcagctca      1320
aggcggccgg gcgcaaggac ctggcggcgt atgaggcgtc ccagccggtc ttccaggaga      1380
acgaggcgat ccagcgcgcg ctgctcctgc agaaggaggc gggctgccga ctcatcgtcg      1440
ttcacgtgag caaccccggc ggcgtggagt tgatccacaa ggcgcagtcg gagggtcagg      1500
acgtgcactg cgagtcaggc cctcagtacc tcaacctcac aatggatgac gccgagaagg      1560
tcggcccgta catgaagatc gccccgccgg tccgttcggc cgagctgaac gccgtcctct      1620
gggagcagct cgagaagggg tacatcgaca cgctcggatc ggatcacggt gggcaccccg      1680
tcgagaacaa ggagggcggc tgggacgaca tctggacggc cagcaacggt gcgctgggac      1740
tggagacgtc gctgccgatg atgctgacca acggcgtcaa caaggccgc gtctcgctgg      1800 agcgactggt cgaggtgatg tgcgagaacc cggcgaagct cttcgggatc tatccgcaga      1860
agggcacgct ccaggtcggc tcggacgccg atctcctcat cctcgatctc gagatcgagg      1920
acaggaaggt ggatgcttcg cagttccgct cgctcctgca ctacagtcca ttcgatggac      1980
ggccggtcac cggcgcgccc gtcctcacga tgatccgtgg aacagtcgtc gcccaggacg      2040
gagagatcct cgtcgaccag gggttcgggc agttcgtgac ccggcgcgac agcgaggtgt      2100
cgtcgtgacg ctgcagcagg cgcgggccga tcgcatcgag gaggagctct ggactctctc      2160
ccgcttctcg gtcgaaggc ccggcgtgac acgtctcacg tacactccgg agcacgccgc      2220
cgcgcgagag gtgatcgtcg ccgccatgca gcggacgggg ctgagcgtcc acgaggacgc      2280
tctcggcaac atcatcggtc ggcgtgaggg gagcgacccc gctctgccgg cgatcgcctt      2340
cggctcgcac ttcgactcgg tccgcaacgg cgggatgttc gacggcaccg cgggcgtggt      2400
gtgcgcgctc gaggctgcga gggtgctgca ggagagcgga tatgtgaacc gtcatcctct      2460
cgaggtcatc gcgatcgtcg aagaggaggg caccgcttc agcagcggca tgctgggcgg      2520
tcgcgcgatc gcggggctcg tgtccgacgc cgatctggac accctggtgg acgaagacgg      2580
cgtgacggtg cgcgaggcgg ccacggcctt cgggctggaa ccgggtgagc tgcggacggc      2640
ggcccgtacg agggatgacc ttcgcgcctt catcgagttg cacatcgagc aggggccgat      2700
cctcgagcag gagaaggtgg agatcggcgt cgtgacgggg atcgtcggtg tccgcgcctt      2760
ccggatcacg gtggagggca ggagcgacca cgccgggacg accccatgc acctgcggca       2820 ggacgcgctg gtgccggcgg cgctcatggt gcgagagatc aatcggttcg tcaacgagat      2880
cgcggacggc acggtggcga ccgtcggcca cctcacggtg accctggtg ggctcaacca       2940 ggttcccggg ggcgtcgagt tcacgctcga tctgcgatcg ccccacgagg agtcgatccg      3000
```

```
gctcctggtc gacaggatcg aggcgatggt ggcagaagtc gccgccgcgg ccggagtcga    3060
ggccgcggtg aacgggttct tcgcgctcag ccctgtcggt ctgtctccgg tggtcgtgga    3120
tcgcgtgcgc gacgcggcgt ccgaactcgg cttcacccat cgcgacatca cgagcggggc    3180
agggcacgac tcgatgttca tcgcccagat caccgacgtc ggaatggtgt tcgtccccag    3240
ccgcgccggg cgaagccatg tgccggagga atggtccgat ttcgacgatc tgcggaaggg    3300
gacggatgtg gtccttcacg tcgtgacggc gcttgaccgg tga                      3343
```

<210> SEQ ID NO 8
<211> LENGTH: 30
<212> TYPE: PRT
<213> ORGANISM: Microbacterium liquefaciens

<400> SEQUENCE: 8

Met Arg Ile His Val Ile Asn Pro Asn Ser Ser Val Asp Leu Thr Asp
1               5                   10                  15

Ala Val Ala Glu Ala Ala Arg Ser Val Val Ser Pro Gly Thr
            20                  25                  30

<210> SEQ ID NO 9
<211> LENGTH: 23
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (6)..(6)
<223> OTHER INFORMATION: n is a, c, t or g
<220> FEATURE:
<221> NAME/KEY: misc_feature
<222> LOCATION: (15)..(15)
<223> OTHER INFORMATION: n is a, c, t or g

<400> SEQUENCE: 9
atgmgnathc aygtnathaa ycc                                             23

<210> SEQ ID NO 10
<211> LENGTH: 32
<212> TYPE: DNA
<213> ORGANISM: Artificial Sequence
<220> FEATURE:
<223> OTHER INFORMATION: synthetic DNA
<220> FEATURE:
<221> NAME/KEY: misc_feature
<222> LOCATION: (12)..(12)
<223> OTHER INFORMATION: n is a, c, t, or g
<220> FEATURE:
<221> NAME/KEY: misc_feature
<222> LOCATION: (30)..(30)
<223> OTHER INFORMATION: n is a, c, t, or g

<400> SEQUENCE: 10
gtggayytga cngaygcagt tgcagargcn gc                                   32

<210> SEQ ID NO 11
<211> LENGTH: 28
<212> TYPE: DNA
<213> ORGANISM: Artificial Sequence
<220> FEATURE:
<223> OTHER INFORMATION: synthetic DNA

<400> SEQUENCE: 11
gccgaattcg cgactggcaa cacgaagg                                        28

```
<210> SEQ ID NO 12
<211> LENGTH: 28
<212> TYPE: DNA
<213> ORGANISM: Artificial Sequence
<220> FEATURE:
<223> OTHER INFORMATION: synthetic DNA

<400> SEQUENCE: 12
cggggatcct tctcgttaga ggtactgc                                              28
```